US009770500B2

(12) United States Patent
Savidge et al.

(10) Patent No.: US 9,770,500 B2
(45) Date of Patent: Sep. 26, 2017

(54) S-NITROSYLATION OF GLUCOSYLATING TOXINS AND USES THEREFOR

(75) Inventors: Tor C. Savidge, League City, TX (US); Jonathan Stamler, Shaker Heights, OH (US)

(73) Assignees: THE BOARD OF REGENTS OF THE UNIVERSITY OF TEXAS SYSTEM, Austin, TX (US); CASE WESTERN RESERVE UNIVERSITY, Austin, TX (US)

( * ) Notice: Subject to any disclaimer, the term of this patent is extended or adjusted under 35 U.S.C. 154(b) by 0 days.

(21) Appl. No.: 13/485,801

(22) Filed: May 31, 2012

(65) Prior Publication Data

US 2013/0005690 A1     Jan. 3, 2013

Related U.S. Application Data

(60) Provisional application No. 61/519,852, filed on May 31, 2011.

(51) Int. Cl.

| | |
|---|---|
| *A61K 31/6615* | (2006.01) |
| *A61K 39/08* | (2006.01) |
| *A61K 45/06* | (2006.01) |
| *A61K 31/198* | (2006.01) |
| *A61K 31/21* | (2006.01) |
| *A61K 38/06* | (2006.01) |

(52) U.S. Cl.
CPC ............ *A61K 39/08* (2013.01); *A61K 31/198* (2013.01); *A61K 31/21* (2013.01); *A61K 31/6615* (2013.01); *A61K 38/063* (2013.01); *A61K 45/06* (2013.01)

(58) Field of Classification Search
CPC ..... A61K 31/21; A61K 31/98; A61K 31/6615
See application file for complete search history.

(56) References Cited

U.S. PATENT DOCUMENTS

2011/0293593 A1*  12/2011  Wallach ................... C12N 9/93
                                                            424/94.5

OTHER PUBLICATIONS

Cariello et al., In vitro amoebicidal activity of S-nitroglutathione and S-nitroso-N-acetylcysteine against . . . , 2010, J. Antimicrob. Chemother. 65(3): 588-591.
Desouza et al., Leishmanicidal activity of primary S-nitrosothiols against Leishmania major and Leishmania amazonensis: Implications for the treatment of cutaneous leishmaniasis. 2006. Nitric Oxide 15: 209-216.
Egerer, et al., "Auto-catalytic Cleavage of Clostridium difficile Toxins A and B Depends on Cysteine Protease Activity", J Biol Chem, 2007, pp. 25314-25321, vol. 282.
Egerer, et al., "Autocatalytic Processing of Clostridium difficile Toxin B", J Biol Chem, 2009, pp. 3389-3395, vol. 284(6).
Egerer and Satchell, Inositol Hexakisphosphate-Induced Autoprocessing of Large Bacterial Protein Toxins. PLoS Pathogens, 2010 6(7): 1-8.
Foster et al., Protein S-nitrosylation in health and disease: a current perspective. 2009, Trends Mol Med, vol. 15(9) 391-404.
Fullner, et al., "MARTX Multifunctional Autoprocessing Repeats-in-Toxin Toxins", Infect Immun, 2007, pp. 5079-5084, vol. 75.
Hess, et al., Nature Rev, 2005, pp. 150-166, vol. 6.
International Search Report and Written Opinion, PCT/US2012/040315, Sep. 7, 2012.
Kelly, et al., "Clostridium Difficile—More Difficult Than Ever", N Engl J Med, 2008, pp. 1932-1940, vol. 359.
Kuehne, et al., "The role of toxin A and toxin B in Clostridium difficile infection", Nature, 2010, pp. 711-713, vol. 467.
Lupardus, et al., "Small Molecule-Induced Allosteric Activation of the Vibrio cholerae RTX Cysteine Protease Domain", Science, 2008, pp. 265-268, vol. 322.
Lyras, et al., "Toxin B is essential for virulence of Clostridium Difficile", Nature, Apr. 30, 2009, pp. 1176-1179, vol. 458.
Ng et al., Clostridium difficile toxin-induced inflammation and intestinal injury are mediated by the inflammasome, 2010. Gastroenterology 139(2): 542-52.
Pei, et al., "CPDadh: A new peptidase family homologous to the cysteine protease domain in bacterial MARTX toxins", Protein Science, 2009, pp. 856-862, vol. 18(4).
Popoff et al., Multifaceted role of Rho, Rac, Cdc42 and Ras in intercellular junctions: lessons from toxins. Biochem Biophys Acta., 2009, vol. 1788: 797-812.
Prochazkova, et al., "Structure-Function Analysis of Inositol Hexakisphosphate-induced Autoprocessing of the Vibrio cholerae Multifunctional Autoprocessing RTX Toxin", J Biol Chem, 2008, pp. 23656-23664, vol. 283.
Reineke, et al., "Autocatalytic cleavage of Clostridium difficile toxin B", Nature, Mar. 22, 2007, pp. 415-419, vol. 446.
Savidge, et al., "Clostridium Difficile Toxin B Is an Inflammatory Enterotoxin in Human Intestin", Gastroenterology, 2003, pp. 413-420, vol. 125(2).
Savidge et al., Host S-nitrosylation inhibits clostridial small molecule-activated glucosylating toxins, 2011 Nat. Med. 17(9): 1136-1141.
Sheahan, et al., "Autoprocessing of the Vibrio cholerae RTX toxin by the cysteine protease domain", EMBO J, 2007, pp. 2552-2561, vol. 26.
Shen et al., Defining an allosteric circuit in the cysteine protease domain of Clostridium difficile toxins, 2011 18(3): 364-372.
Zaman et al., S-nitrosylating agents: a novel class of compounds that increase cystic fibrosis transmembrane conductance regulator expression and maturation in epithelial cells. 2006, Mol. Pharmacol. 70(4): 1435-1442.

* cited by examiner

*Primary Examiner* — Zohreh Fay
(74) *Attorney, Agent, or Firm* — Norton Rose Fulbright US LLP

(57) ABSTRACT

Provided herein are methods for ameliorating the pathophysiology cysteine protease exotoxin comprising the step of administering to said individual an effective dose of an S-nitrosylating agent and an inositol phosphate or analog thereof.

5 Claims, 19 Drawing Sheets

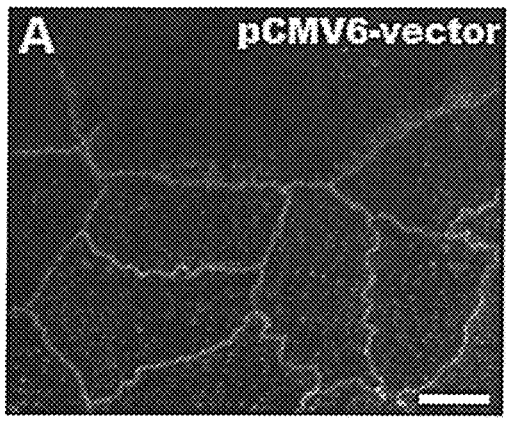
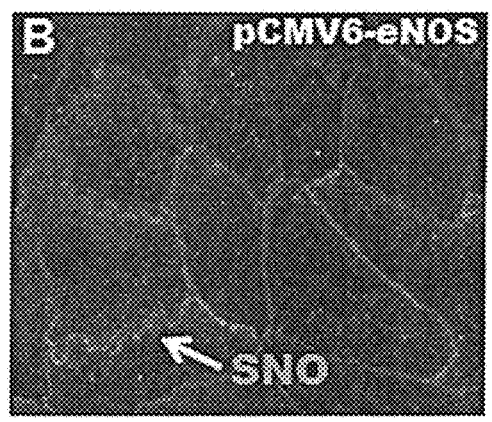
FIG. 2A  FIG. 2B
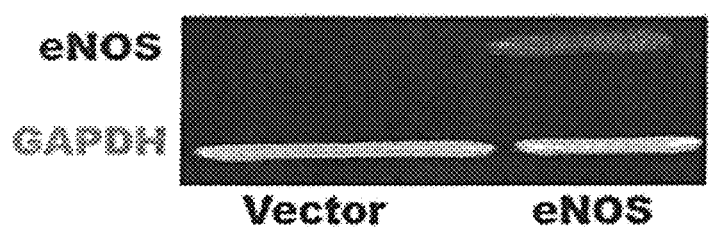
FIG. 2C
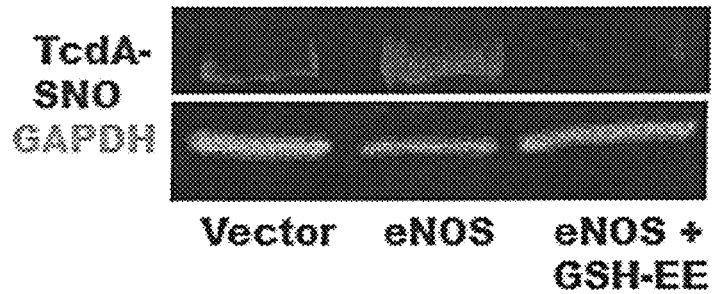
FIG. 2D

S-NITROSYLATION OF GLUCOSYLATING TOXINS AND USES THEREFOR

PRIORITY CLAIM

This application claims priority to U.S. Provisional Patent Application Ser. No. 61/519,852 filed May 31, 2011, which is incorporated herein by reference in its entirety.

STATEMENT REGARDING FEDERALLY FUNDED RESEARCH

This invention was made with government support under R01AI088748, N01AI30050, R01DK084509, K01DK076549, R21-DK078032-01, R01-HL059130, R01-HL091876, R01HL095463, HL075443-06A and 1UL1RR029876-01 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

The present invention relates generally to the fields of microbiology, pharmacology, and medicine. More specifically, the present invention relates to allosteric therapeutics for microbial infections and associated glucosylating toxins.

_Clostridium difficile_ (_C. difficile_) infection (CDI) is the most prevalent cause of hospital-acquired infectious diarrhea and life-threatening colitis worldwide (Kelly et al., _N Engl J Med_ 359:1932-1940 (2008)). Two large exotoxins, TcdA (308 kDa) and TcdB (270 kDa), are secreted from the majority of _C. difficile_ bacterial strains that cause disease in humans, and there is little ambiguity that these toxins are pathogenic since toxin-deficient strains are avirulent (Savidge et al., _Gastroenterology_ 125:413-20 (2003); Lyras et al. _Nature_ 458:1176-79 (2009); Kuehne et al., _Nature_ 467:711-13 (2010)). The clostridial glucosylating toxins and the multifunctional autoprocessing repeats-in-toxins (MARTX) share a common virulence mechanism for cell entry that represents a potential target for therapeutic intervention (Fullner et al., _Infect Immun_ 75: 5079-84 (2007); Sheahan et al., _EMBO J_ 26: 2552-61 (2007); Egerer et al., _J Biol Chem_ 282: 25314-21 (2007); Pei et al., _Protein Science_ 18: 856-62 (2009)). Cellular internalization of these exotoxins is dependent on cytosolic inositol hexakisphosphate (InsP$_6$) allosteric cofactor, which activates an autocatalytic cysteine protease domain to facilitate toxin self-cleavage (Reineke et al., _Nature_ 446:415-19 (2007); Prochazkova et al., _J Biol Chem_ 283: 23656-64 (2008); Lupardus et al., _Science_ 322:265-68 (2008); Egerer et al., _J Biol Chem_ 284:3389-95 (2009)). Intracellular release of the smaller N-terminus glucosyltransferase effector domain results in the mono-O glucosylation of small GTPases of the Rho family, including RhoA, Rad, and Cdc42 (Popoff et al., _Biochim Biophys Acta._ 88:797-812 (2009)). Glucosylation of Rho proteins inhibits their molecular switch function, thus blocking Rho GTPase-dependent signaling in intestinal epithelial cells, leading to alterations in the actin cytoskeleton, fluid secretion, acute inflammation, and necrosis of the colonic mucosa.

Host defense mechanisms that might be employed to protect against the clostridial glucosylating toxins are not well defined, although _C. difficile_ toxins are potent inducers of nitric oxide (NO), which is known to be protective against these toxins (Ng et al., _Gastroenterology_ Apr. 13 (2010)). However, the precise molecular mechanism for the protective effects of NO remains unknown. Some diverse signaling cascades associated with NO production are attributed to S-nitrosothiol (SNO) species that act via covalent modification of specific cysteine residues in target molecules (S-nitrosylation)(Hess, et al., _Nature Rev_ 6:150-166 (2005)) and aberrant S-nitrosylation may play a role in disease-etiology (M W et al., _Trends Mol Med_ 15: 391-404 (2009)).

There is a recognized need in the art for alternative therapies for infections by toxins such as _Clostridium difficile_. Specifically, the prior art is deficient in treatments for glucosylating toxin infections. The present invention fulfills this long-standing need and desire in the art.

SUMMARY

Certain embodiments are directed to S-nitrosylation of pathologic cysteine proteases, such as autocatalytic exotoxins (e.g., CGTs, gingipains, CPD$_{MARTX}$, and CPDadh). In certain aspects, the methods and compositions described herein provide protection against or ameliorate the effects of cellular intoxication by pathogenic cysteine proteases. Studies using _C. difficile_, provide evidence for cross-talk between inositol phosphate cofactors and NO signaling. In certain aspects, compositions and methods described herein use inositol phosphates to enhance S-nitrosothiol action as a therapeutic for pathologies associated with various pathogenic cysteine proteases. Pathologies include bacterial induced colitis and inflammation. In certain aspects, the methods and composition described herein provide for a therapeutic allostery against pathologic cysteine proteases, such as the clostridial small molecule-activated glucosylating toxins (CGTs).

Pathogenic cysteine proteases are autocatalytic polypeptides that contain a cysteine protease domain (CPD). Cleavage of the polypeptide releases one or more polypeptide domains that result in one or more pathologic conditions in a subject (e.g., toxic shock, diarrhea, colitis, inflammation, and the like). Amino acids 576 to 756 of SEQ ID NO:1 (_C. difficile_ TcdA) provide one example of a CPD, other similar domains can be identified by using various search and analysis algorithms. Other target polypeptides can have a CPD domain that is 30, 40, 50, 60, 70, 80, 90, 95, or 100% identical to the CPD of TcdA.

Certain embodiments are directed to methods for ameliorating the pathophysiology of a microbial cysteine protease exotoxin in a subject comprising, administering to the subject an effective dose of an S-nitrosylating agent and an inositol phosphate or analog thereof. In certain aspects, the exotoxin is a _Clostridium_ exotoxin, such as a _Clostridium difficile_, _Clostridium sordellii_, _Clostridium novyi_, _Clostridium botulinum_, _Clostridium perfringens_, or _Clostridium tetani_ exotoxin. In a further aspect the exotoxin can be _Vibrio cholera_ RTX, gingipain, CPD$_{MARTX}$, or CDP$_{adh}$ exotoxin.

In certain embodiments the inositol phosphate can be a hexakisphosphate, inositol pyrophosphate or analog thereof. The inositol phosphate or analog thereof can be administered in an amount of about 1, 10, 20, 30, 40, 50, 60, 70, 80, 90 μM to about 1, 2, 3, 4, 5, 6, 7, 8, 9, 10 mM, including all values and ranges there between.

S-nitrosylation is a post-translational modification of a protein that is mediated by reaction with nitric oxide. As used herein the term "nitrosylation" refers to the addition of NO to a thiol group (SH), oxygen, carbon or nitrogen by chemical means. An "S-nitrosylating agent" refers to a compound that can function in vivo to react with protein thiol groups, transferring a NO group to the thiol to form an S-nitrosothiol. Suitable nitrosylating agents are disclosed in Feelisch and Stamler, "Donors of Nitrogen Oxides", Methods in Nitric Oxide Research edited by Feelisch and Stamler, (John Wiley & Sons) (1996), the entire teachings of which are hereby incorporated into this application by reference. S-nitrosylating agents include nitrosylators that directly nitrosylate (e.g., GSNO), potentiators that potentiate nitrosylation (e.g., N-acetyl cysteine (NAC)), and nitric oxide generators that produce nitrosylators (nitrite plus GSH or NAC), as well as esters and/or salts thereof. S-nitrosylating agents include acidic nitrite, alkyl nitrate, nitrosyl chloride, ethyl nitrite, amyl nitrite, glutathione (GSH), S-nitrosoglutathione (GSNO), S-nitrosocysteinyl glycine, S-nitrosocysteine, N-acetyl cysteine, S-nitroso-N-acetyl cysteine, nitroglycerine, nitroprusside, nitric oxide, S-nitrosohemoglobin, S-nitrosoalbumin, S-nitroso-N-acetylpenicillamine, S-nitrosocysteine, S-nitroso-gamma-methyl-L-homocysteine, S-nitroso-L-homocysteine, S-nitroso-gamma-thio-L-leucine and S-nitroso-δ-thio-L-leucine and S-nitrosoalbumin. In certain aspects, the S-nitrosylating agent is a phytocheletin, i.e., a glutathione oligomer. In certain aspects, the S-nitrosylating agent comprises (a) a nitrate and (b) glutathione and/or N-acetylcysteine. In a further aspect the nitrate is an organic nitrate, such as ethyl nitrite or amyl nitrite. In certain aspects, the S-nitrosylating agent is administered in an amount of about 1, 10, 20, 30, 40, 50, 60, 70, 80, 90 µM to about 0.1, 0.5, 1, 2, 3, 4, 5 mM, including all values and ranges there between.

Certain embodiments are directed to methods of treating a Clostridium infection in a subject comprising administering to the subject an effective dose of an S-nitrosylating agent and an inositol phosphate or analog thereof.

Other embodiments are directed to methods of reducing or preventing the effects of a pathogenic cysteine protease in a subject. In certain aspects, the subject has an infection, wherein the infection results in the production of pathogenic cysteine proteases. In a further aspect the cysteine protease is a glucosylating toxin. Certain embodiments are directed to methods of treating a subject that include administering to a subject an effective amount of an inositol phosphate and an S-nitrosylating agent, wherein a pathogenic cysteine protease is inactivated by S-nitrosylation.

Further embodiments are directed to methods of treating a subject having an infection that produces a glucosylating toxin, comprising the steps of administering to a subject an effective dose of (a) an agent that causes or increases S-nitrosylation of the toxin and (b) an inositol phosphate or analog thereof.

Certain embodiments are directed to pharmaceutical compositions comprising an S-nitrosylating agent and an inositol phosphate or analog thereof. In certain aspects, the inositol phosphate is a hexakisphosphate, or inositol pyrophosphate. In a further aspect, the S-nitrosylating agent is S-nitrosoglutathione, nitrite, glutathione, N-acetylcysteine, a GSNO reductase inhibitor, N-acetylcysteine, and/or phytocheletins.

In certain aspects, the S-nitrosylating agent and the inositol phosphate or analog thereof are comprised in the same pharmaceutical composition. In certain aspects, the composition is formulated for delivery to the gastrointestinal tract. In a further aspect, the composition can be formulated for delivery of the active ingredients to the mouth, throat, esophagus, stomach, small intestine, ileum, jejunum, duodenum, large intestine, cecum, ascending colon, transverse colon, descending colon, sigmoid colon, or rectum.

In certain aspects, a pharmaceutical composition is a sustained release composition comprising an agent that causes or increases S-nitrosylation of a glucosylating toxin; and an inositol phosphate. Most preferably, the composition is formulated for release in gastrointestinal tract, e.g., the mouth, esophagus, stomach, the small intestine, the ileum, the jejunum, the duodenum, the large intestine, the cecum, the ascending colon, the transverse colon, the descending colon, the sigmoid colon or the rectum. In one preferred aspect, the agent is S-nitrosoglutathione (GSNO).

In one embodiment of the present invention, there is provided a method of treating infection in an individual associated with a glucosylating toxin, comprising the step of administering to said individual an effective dose of an agent that causes or increases S-nitrosylation of said toxin. In one preferred aspect, the agent is S-nitrosoglutathione. The S-nitrosoglutathione may be administered in an effective concentration depending upon the result desired, for example, of about 1 µM to about 1 mM. Preferably, this agent activates or enhances local GSNO concentrations.

In one aspect, the toxin is from a member of the genus Clostridium. Representative species in the genus Clostridium include but are not limited to Clostridium difficile, Clostridium sordellii, Clostridium novyi, Clostridium botulinum, Clostridium perfringens and Clostridium tetani. In another aspect, the toxin is Vibrio cholerae $CPD_{RTX}$, the gingipains and structurally similar cysteine regulated domains belonging to the $CPD_{MARTX}$ and CPDadh superfamilies.

The compositions and methods described herein can be used to neutralize a toxin either in vitro or in vivo. For example, the toxins, or the bacteria producing such toxins, are contacted with one or more of the compositions described herein. Effectiveness may be determined by an assay to determine if the toxin cleavage product is present.

As such, the present invention also provides methods for treating an infection, such as but not limited to Clostridium difficile infection in a subject. The compounds provided may be administered one or more times to a subject in need of such treatment. Dosage formulations may comprise conventional non-toxic, physiologically or pharmaceutically acceptable carriers or vehicles suitable for the method of administration. These compounds or pharmaceutical compositions thereof may be administered independently one or more times to achieve, maintain or improve upon a pharmacologic or therapeutic effect derived from these compounds or other agents suitable for C. difficile infection being treated. It is well within the skill of an artisan to determine dosage or whether a suitable dosage comprises a single administered dose or multiple administered doses. An appropriate dosage depends on the subject's health, the progression or remission or at risk status of the infection, the route of administration and the formulation used. Preferably, these compounds may be administered in an oral formulation, although the scope of the invention does not limit administration to an oral route. Moreover, the methods and compositions provided herein are applicable to conditions not classified as infections.

As used herein, the term "contacting" refers to any suitable method of bringing compound, e.g., inositol phosphate, into contact with a Clostridium toxin or the bacterial cell producing the same. In vitro or ex vivo this is achieved by exposing the compound to the toxin and/or bacteria in a suitable medium. For in vivo applications, any known method of administration is suitable.

As used herein, the term "subject" refers to any recipient or individual administered a composition as described herein that are effective as therapeutics or inhibitors against a pathologic condition associated with cysteine proteases.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 1A-1C: A murine toxigenic ileal-loop model was used to demonstrate TcdA-induced pathology (FIG. 1B) compared with vehicle (veh) control (FIG. 1A) and TcdA-SNO (FIG. 1C) treatment groups (scale bar=50 μm). Analysis of tissue sections revealed that TcdA (10 μg) induced epithelial cell damage, neutrophil tissue infiltration and edema of the intestinal mucosa were reduced in TcdA-SNO treated animals. FIG. 1D: Increased tissue GSNO levels correlate with elevated iNOS expression in ileal-loops exposed to TcdA for 4 hrs. FIGS. 1E and 1F: SNO-immunofluorescence showing abundant epithelial S-nitrosylation in human colitis (FIG. 1F) but not in histologically normal colon (FIG. 1E) where SNOs are largely confined to lamina propria cells (arrows illustrate brush border membrane; SNOs; DAPI nuclear counter-stain; scale bar=20 mm). This finding confirms that SNO-proteins are increased in human colitis. FIG. 1G: Cysteine saturation fluorescence assay demonstrates in situ S-nitrosylation of TcdA in intoxicated ileal loops (protein spot identified by mass spectrometry). FIG. 1H: Biotin-switch assay using a C-terminus specific anti-TcdA monoclonal antibody (clone A1H3) demonstrates exotoxin S-nitrosylation in tissue lysates from TcdA exposed ileal loops, but not in vehicle controls. Treatment of toxin exposed mucosal extracts with DTT (1 mM) prior to the biotin-switch eliminated TcdA-SNO.

FIGS. 2A-2I. S-nitrosylation inhibits *C. difficile* toxin activity. FIGS. 2A-2B: Anti-SNO immunofluorescence showing that Caco-2 cells transfected with pCMV6-eNOS express higher levels of membrane-associated SNO-proteins that co-localize with anti-zonula occludens (ZO-1) immunoreactivity (Scale bar=10 μM). FIG. 2C: eNOS expression is specific to pCMV60-eNOS transfected Caco-2 cells. The transfection efficiency of a pCMV6-gfp vector in Caco-2 cells was approximately 50%. FIG. 2D: Anti-SNO blot (non-reducing conditions) shows that TcdA is preferentially S-nitrosylated in pCMV60-eNOS transfected Caco-2 cells and S-nitrosylation is diminished following membrane permeable GSH-ethyl ester (GSH-EE) treatment. Low levels of toxin S-nitrosylation is also evident in vector control cells, reflecting lower endogenous SNO. Equal protein loading is demonstrated by GAPDH labeling. FIGS. 2E-2F: TcdB induced significantly less cell rounding in vector control (FIG. 2E) vs. eNOS (FIG. 2F) transfected Caco-2 cells (71.1+14.9 vs. 26.5+8.2%, respectively; +SEM, n=3; $p<0.05$, Mann-Whitney U-test on ranks) (Scale bar=25 μM). FIG. 2G: MTT cytotoxicity assay showing significant cytoprotection of pCMV6-eNOS expressing Caco-2 cells against TcdB (3.7 nM for a 10 min exposure). This protection is reversed by GSH-EE and by L-NAME treatment ($p<0.05$, compared to vector control (*) and eNOS (#) transfected cells respectively; Mann-Whitney U-test on ranks) FIG. 2H: Toxin-induced Rac1 glucosylation in vector and eNOS transfected Caco-2 cells. Cells were exposed to a 10 min TcdB pulse (3.7 nM) and cellular lysates were examined for non-glucosylated and total Rac1 after 60 min. eNOS-Caco-2 cells showed significantly less toxin-induced Rac1 glucosylation as compared with vector-controls (65.8+11.4 vs. 34.3+10.7%, respectively; n=3; $p<0.05$, Mann-Whitney U-test on ranks) FIG. 2I: Toxin-induced Rac1 glucosylation in wild type (Wt) and iNOS deficient murine peritoneal macrophages. Macrophages were first activated with 20 ng IL1-γ for 24 hrs prior to toxin exposure. Cells were exposed to a 10 min TcdB pulse (3.7 nM) and cell lysates were examined for non-glucosylated and total Rac1 after 60 min. iNOS deficient macrophages showed significantly more Rac1 glucosylation as compared with wild type cells (56.5+11.2 vs. 31.3+5.2%, respectively; +SEM, n=3; $p<0.05$, Mann-Whitney U-test on ranks).

FIGS. 3A-3D. S-nitrosylated toxins in *C. difficile* patient stool samples. FIG. 3A: Biotin-switch assay showing S-nitrosylated toxin (TcdA-SNO) labeled with IR800-streptavidin dye (right inset). MTT cell viability assays (550 nm) demonstrate that toxin S-nitrosylation significantly attenuates TcdA-induced cytotoxicity in Caco-2 cells (*, $p<0.05$; Mann-Whitney U-test on ranks) FIG. 3B: Patient stool (n=8) samples positive for TcdA (antibody A1H3), and confirmed by cytotoxicity assay. FIG. 3C: Cytotoxicity was assessed by mixing mRG1 cells with enhancing antibody A1H3, with or without coded human stool samples (examples shown are UTMB10 (positive) and UTMB14 (negative), 50× dilution in PBS) in the presence or absence of neutralizing antibody (He et al., *J Microbiol Methods* 78:97-100 (2009)). FIG. 3D: Ratios of TcdA-SNO vs. total TcdA show a negative relationship between toxin S-nitrosylation and cytotoxicity. TcdA-SNO was first immunoprecipitated from stool samples using an anti-nitrosocysteinyl antibody and samples were then probed for TcdA (antibody A1H3).

FIG. 4A: N-terminus extended cysteine protease domain model for TcdB (based on TcdB (3PA8.pdb) and RTX (3FZY.pdb) crystal structures showing the flexible p-flap abutting the bound allosteric ligand $InsP_6$. FIG. 4B: S-nitrosylation of TcdA significantly inhibits $InsP_6$ binding and is reversed by UV irradiation, which cleaves the SNO bond. As a positive control, $InsP_6$ binding to deoxygenated hemoglobin, a well established means of allosteric modulation, confirms a binding affinity of >1.6 nM/mg protein. $InsP_6$ binding to hemoglobin is inhibited by primary amide-biotinylation which blocks access to the $InsP_6$ binding site. FIG. 4C: Simulated docking of $InsP_7$ binding to the allosteric pocket in TcdB using Autodock 4.0 shows several poses that closely match $InsP_6$ bound in the crystal structure (comparable results are determined for TcdA and $RTX_{VC}$). Calculated binding energies for $InsP_6$ and $InsP_7$ to TcdB are −21.60 and −23.01 kcal mol$^{-1}$, respectively. FIG. 4D: In vitro cleavage assays demonstrate that $InsP_7$ (100 µM) has a significantly greater activity for TcdB than $InsP_6$ ($p<001$, Mann Whitney U-test for ranks, n=3). r-InsP7 ((rac1)-1(3)-PP-(2,3,4,5,6)InsP$_5$) and m-InsP7 (D-myo-5-PP-(1,2,3,4,6)InsP$_5$) cleavage activities for TcdB were not significantly different. FIG. 4E: SNO-immunoblot showing that $InsP_6$ induces S-nitrosylation of TcdB. DTT (1 mM) inhibits S-nitrosylation by $InsP_6$ (100 µl) (anti-TcdB labeling with the C-terminus targeting monoclonal antibody 5A8-E11). FIG. 4F: SNO-immunoblot showing that $InsP_6$ induced S-nitrosylation is markedly reduced in the TcdB Cys698Ser toxin mutant. FIG. 4G: $InsP_6$ induced TcdB autocleavage is dose-dependently inhibited by simultaneous addition of GSNO. FIG. 4H: SDS-PAGE showing unprocessed (270 kDa) and processed TcdB cleavage products (207 & 63 kDa). TcdB autocleavage is inhibited by the simultaneous addition of GSNO (100 µM), but is potentiated by GSH (100 µM). No significant toxin autocleavage is evident in the presence of GSH or DTT alone. Real-time BiaCore toxin cleavage assays demonstrated that GSNO rapidly inhibits TcdB autocleavage.

FIG. 5A: Surface rendering of the TcdB cysteine protease domain (3PA8.pdb) showing the exposed S-nitrosylation consensus motif E743-C698-H653. In silico docking of GSNO to this crystal structure using Autodock 4.0 demonstrates that the lowest energy cluster associates with the active site, where the S—NO bond aligns to the catalytic cysteine. FIG. 5B: Crystal structures of TcdA, $RTX_{VC}$ and gingipain demonstrate that this S-nitrosylation motif is structurally conserved amongst a diverse array of microbial cysteine protease domains. FIG. 5C: $InsP_6$ induced S-nitrosylation of TcdB cysteine protease domain mutants. SNO-immunoblot shows S-nitrosylation results for TcdB His653Ala, Glu743Ala and Cys698Ser mutants in the presence of GSNO and $InsP_6$ (100 µM; 10 min at 37° C.). FIG. 5D: Analysis of the $RTX_{VC}$ cysteine protease domain crystal structure with an intact elongated N-terminus (3FZY.pdb), demonstrates an extensive network of interconnecting hydrogen bonds within the active site (dotted lines). This interconnecting hydrogen bond network is conserved in TcdA and TcdB. FIG. 5E: Catalytic activity of TcdB cysteine protease domain mutants. SDS-PAGE showing $InsP_6$ induced cleavage (100 µM for 60 min) of TcdB Cys698Ser, Glu743Ala, and His653Ala mutants. The Cys698Ser and His653Ala mutants are catalytically inactive, whereas self-cleavage is greatly enhanced in the Glu743Ala mutant. FIG. 5F: $InsP_6$ dose-response studies (10 min incubation, using an N-terminus specific TcdB VHH single chain antibody (JC12) for assay of cleavage activity) demonstrated that the Glu743Ala mutant is approximately two orders of magnitude (FIG. 5G) more sensitive to $InsP_6$ induced cleavage than the wild type toxin.

FIG. 6A: Biotin-switch assay showing increased protein S-nitrosylation in Caco-2 cells incubated with GSNO (100 µM for 30 min). FIG. 6B: Dose-response curves for GSNO inhibition of TcdB (3.7 nM; 10 min incubation) in the absence (closed circles) or presence of GSH (1 mM; open circles) and $InsP_6$ (100 µM; filled triangles). FIG. 6C: GSNO (10 mg/kg in 0.1 ml) inhibits TcdA (10 µg) induced fluid secretion in murine ileal loops and this protective effect is enhanced by allosteric effector $InsP_6$ (1 mM; n>6 group; p<0.05 compared with vehicle control (*) and TcdA-vehicle (#), respectively; ANOVA on ranks) FIG. 6D: Exposing mouse ileal loops to TcdA (10 µg) for 4 hrs induced a significant accumulation of gene transcripts for TNF-α and IL-1γ. GSNO significantly attenuated this response and inhibition was potentiated by $InsP_6$ (1 mM; p<0.05 compared with vehicle control (*) and TcdA-vehicle (#) treated loops respectively; ANOVA on ranks) FIG. 6E: survival plots of C57BL/6 mice inoculated intragastrically with 10$^6$ *C. difficile* VPI 10463 and orally gavaged with GSNO (10 mg/kg/day); GSNO/$InsP_6$ (10 & 0.25 mg/kg/day, respectively), $InsP_6$ (0.25 mg/kg/day) or vancomycin (50 mg/kg/day; n=12 per group). GSNO/$InsP_6$ (10 & 0.25 mg/kg/day, respectively) was also delivered continuously by mini-osmotic pumps via an intracecal catheter. FIG. 6F: Intracecal GSNO/$InsP_6$ administration conferred significant protection from *C. difficile* infection, with survival rates greater than 80% (n=12/group; survival at Day 4; p<0.05 compared with vehicle control (*) and GSNO (#) respectively; ANOVA on ranks).

DESCRIPTION

Figures 1A, 1B, 1C:
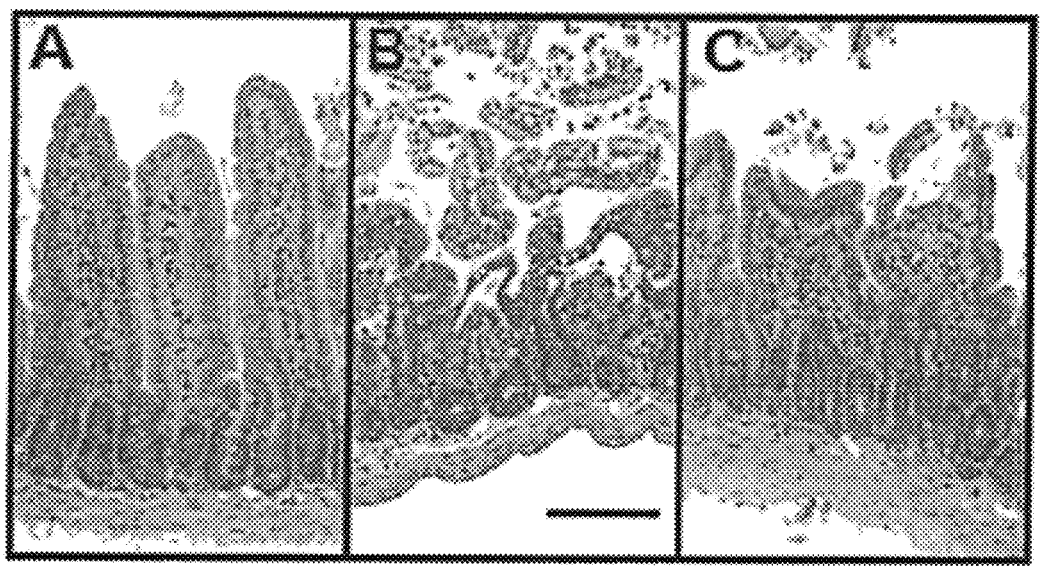
FIGS. 1A-1H. *C. difficile* toxins are among the proteins S-nitrosylated in vivo.

The emergence of a hypervirulent form of *C. difficile* (NAP1/027) has resulted in a global increase in *C. difficile* infection, due in part to the high levels of toxin produced by this strain (Kelly et al., *N Engl J Med* 359:1932-40 (2008); Savidge et al., *Gastroenterology* 125:413-20 (2003); Lyras et al. *Nature* 458: 1176-79 (2009); Kuehne et al., *Nature* 467:711-13 (2010)). Examples provided herein demonstrate that GSNO is an endogenous inhibitor of *C. difficile* infection, which acts in significant part by S-nitrosylation of toxin active site thiol. GSNO accumulation during *C. difficile* infection reaches levels that inactivate the toxin in vitro and in vivo, and GSNO can be used therapeutically to inhibit fulminant disease. GSNO is well tolerated in humans, and is a multifaceted protective agent that exhibits broad-spectrum anti-microbial activity (Hess et al., *Nature Rev* 6: 150-166 (2005); M W et al., *Trends Mol Med* 15: 391-404 (2009)). S-nitrosylating agents can be used as a basis of a new treatment for *C. difficile* infection.

Hyper- or hypo-nitrosylation of specific proteins may represent disease-modifying events (Benhar et al., *Science*

320:1050-54 (2008)). A major challenge in NO therapeutics is to control the nitrosylation of specific protein targets that correlate best with pathophysiology. Recent in vitro studies have raised the idea that various allosteric effectors may play a role in conferring NO specificity (M W et al., *Trends Mol Med* 15: 391-404 (2009)). The present invention provides physiological context for this principle by showing that InsP$_6$ and InsP$_7$ are specificity-determinants of toxin cysteine protease S-nitrosylation. More generally, allosteric modulation of S-nitrosylation suggests new therapeutic approaches to regulating nitrosylation of disease-modifying molecular targets.

The toxin cysteine protease structurally resembles the caspase protease domain family, which is also subject to S-nitrosylation (M W et al., *Trends Mol Med* 15: 391-404 (2009)). Notably, inhibition of pro-caspase 3 by S-nitrosylation entails both orthosteric (active site) and allosteric mechanisms (Matsumoto et al. *Science* 301: 657-61 (2003)). Pro-caspase 3 is maintained in the S-nitrosylated and inactive state in the mitochondria but not in the cytosol. Although the basis of maintained S-nitrosylation in the mitochondria is not known (Benhar et al., *Science* 320:1050-54 (2008)), plasma membrane/endosome compartments may provide privileged access to allosteric cofactors that would influence S-nitrosylation levels. S-nitrosylation is already known to suppress parasitic and viral pathogenesis by inhibiting cysteine protease-regulated metabolism and reproductive function (M W et al., *Trends Mol Med* 15: 391-404 (2009); Saura et al. *Immunity* 10: 21-28 (1999)). However, host S-nitrosylation has not been shown to directly inhibit microbial exotoxin activity, and the dual protective mechanism involving catalytic Cys inhibition and allosteric activation is unique. In particular cross-talk between inositol phosphates and NO has not previously been described. Given the recent emergence of an extensive array of new microbial proteins ($CPD_{MARTX}$ and $CPD_{adh}$) that appear to require an active cysteine protease for host cell adhesion and entry (Pei et al., *Protein Science* 18: 856-62 (2009)), S-nitrosylation may represent a universal host defense mechanism.

I. Pathogenic Cysteine Proteases

Various pathogens, such as those of the genus *Clostridium*, produce highly potent pathogenic cysteine proteases, such as clostridial glucosylating toxins (CGTs). CGTs are single-chain proteins subdivided into at least four functional domains (See Jank and Aktories, *Trends Microbiol.* 16:222-29 (2008), which is incorporated herein by reference). Binding of the toxins to cell surface receptors is mediated by a C-terminal region, including a series of repetitive oligopeptides. After uptake of the toxins, a central region mediates translocation from endosomes into the cytosol. The glucosyltransferase domain is located at the N-terminal end of the toxins. The glucosyltransferase domain is released into the cytosol by auto-catalytic cleavage induced by an adjacent cysteine protease domain (CPD). (See FIG. 1 of Egerer et al., *J. Biol. Chem.* 282(35):25314-21 (2007), which is incorporated herein by reference in its entirety particularly).

The CPD domain is a member of the peptidase C80 family and is represented in the National Center for Biotechnology Information (NCBI) Conserved Domain database under accession pfam11713 or accession number PF11713 of the Pfam database of the Sanger Institute, the information associate with both of these database accession numbers are incorporated herein by reference as of the filing date of the current application. Amino acids 576 to 756 of SEQ ID NO:1 provide an example of a CPD, other similar domains can be identified by using various search algorithms.

Clostridial Glucosylating Toxins (CGT) include, but are not limited to *Clostridium sordellii* lethal toxin, *C. novyi* α-toxin, *C. difficile* toxin A, and *C. difficile* toxin B. This group of toxins are major virulence factors. *C. difficile* toxins A and B cause antibiotic-associated diarrhea and pseudomembranous colitis, *C. sordellii* lethal toxin is implicated in toxic-shock syndrome, and *C. novyi* α-toxin plays a pathogenetic role in gas gangrene syndrome.

CPD domains are also found in the Multifunctional Autoprocessing RTX-like (MARTX) polypeptides, such as those found in *Vibrio cholerae, Vibrio vulnificus*, and *Vibrio anguillarum.*

Polypeptides classified as CPDadh polypeptides also contain CPD domains (See Pei et al. Feb. 10, 2009 at proteinscience.org, which is incorporated herein by reference in its entirety). CPDadh polypeptides are homologous to $CPD_{MARTX}$ polypeptides. CPDadh polypeptides are found in bacteria and eukaryotes. In certain aspects, CPDadh can be limited to bacterial CPDadh. In a further aspect, CPDadh polypeptides can be limited to pathogenic bacterial CPDadh polypeptides. The pathogenic CPDadh polypeptides can include those polypeptides that are allosterically regulated by inositol phosphate or analogs thereof. Examples of CPDadh polypeptides include GenBank accession numbers gi89075996 and gi90578280, each of which is incorporated herein by reference.

Members of the gingipain polypeptide family contain CPD domains. Gingipain is a protease secreted by *Porphyromonas gingivalis*. *Porphyromonas gingivalis* belongs to the phylum *Bacteroidetes* and is a non-motile, Gram-negative, rod-shaped, anaerobic pathogenic bacterium. *P. gingivalis* is found in the oral cavity, where it is implicated in certain forms of periodontal disease, as well as the upper gastrointestinal tract, respiratory tract, and in the colon. Additionally *P. gingivalis* has been linked to rheumatoid arthritis.

II. S-Nitrosylating Agents

S-nitrosylating agents include agents that generate or increase GSNO in situ. In one embodiment, the composition comprises nitrite. The nitrite is either an organic nitrite or an inorganic nitrite. Organic nitrite does not require acidic conditions to form GSNO and is much more potent; but inorganic nitrite can be used if conditions are acidic and amounts are larger (e.g., up to 100 μM-50 mM). The organic nitrite may be, for example, ethyl nitrite or amyl nitrite. In one embodiment, the composition contains a nitrite and glutathione. In another embodiment, the composition contains a nitrite and N-acetylcysteine. In another embodiment, the composition contains a nitrite and a phytocheletin or hydrogen sulfide. In one aspect, the S-nitrosylating agents (either individually or combined) are present in the composition/administered in an amount of about 1 μM to about 1 mM.

In any of the embodiments described herein, the composition may further comprise one or more inositol phosphates or analogs thereof. The combination of inositol phosphates (e.g., IP6 and IP7 and there analogs) with S-nitrosylating agents (such as GSNO and GSNO-generating agents) demonstrate synergistic effects (therapeutic allostery).

III. Inositol Phosphates and Analogs Thereof

In certain aspects a composition or method includes one or more inositol phosphates or analogs thereof. Representative inositol phosphates include but are not limited to inositol hexakisphosphate, inositol pyrophosphate, or an inositol phosphate analog. In one aspect, the inositol phosphates and analogs thereof (either individually or combined) are present in the composition/administered in an amount of about 1 µM to about 1 mM.

Certain aspects are directed to inositol hexakisphosphate analogs (See, U.S. Provisional Patent Application Ser. No. 61/516,639 filed Apr. 6, 2011 and U.S. patent application Ser. No. 13/441,017 filed Apr. 6, 2012, both of which are incorporated herein by reference in their entirety. In certain aspects, an inositol hexakisphosphate analog will be an allosteric enhancer of *C. difficile* exotoxin, or similar proteins, that results in a conformational change in the protein, which in turn provides greater access for S-nitrosylation of an active site cysteine. In further aspects, the analog will be a degradation resistant (e.g., phytase resistant) allosteric enhancer of *C. difficile* exotoxin or similar proteins. In certain embodiments the derivative or analog compound has a chemical structure of Formula I:

Formula I $$\begin{array}{c} OR_2 \\ R_3O \overset{}{\diagup} \diagdown OR_1 \\ R_4O \overset{}{\diagup} \diagdown OR_6 \\ OR_5 \end{array}$$

where $R_1$-$R_6$ independently are —PO(OH)$_2$, —PS(OH)$_2$, —PSe(OH)$_2$, —AsO$_3$, or (NO)$_{1-2}$, or NO associated with —PO(OH)$_2$ (i.e., —PO(OH)$_2$NO). In certain aspects, at least one of $R_1$-$R_6$ is —PS(OH)$_2$, —PSe(OH)$_2$, or NO associated with —PO(OH)$_2$ (i.e., PO(OH)$_2$NO). In certain aspects $R_1$ and $R_3$ are not both —PSe(OH)$_2$ or —PS(OH)$_2$ when $R_2$, $R_4$, $R_5$, $R_6$ are —PO(OH)$_2$. In certain aspects, $R_1$ is not —PS(OH)$_2$ or —PSe(OH)$_2$ if $R_2$-$R_6$ are —PO(OH)$_2$. In further aspects, the analog can be a pharmacologically effective salt of the compounds described herein. In other aspects, the analog can be a derivative, such as the pyrophosphates IP7 and IP8.

In certain embodiments, the inositol analog is a myo-inositol analog. In further aspects, the inositol analog is a neo-inositol analog. In still further aspects, the inositol analog is a D-chiro-inositol analog. In further aspects, the inositol analog is a L-chiro-inositol analog. In certain aspects, the inositol analog is a muco-inositol analog. In still further aspects, the inositol analog is an allo-inositol analog. In still further aspects, the inositol analog is a scyllo-inositol analog. In yet further aspects, the inositol analog is an epi-inositol analog. In certain aspects, the inositol analog is a cis-inositol analog.

As used herein, "analog" refers to a chemical compound that is structurally similar to a parent compound, but differs in composition (e.g., differs by appended functional groups or substitutions). The analog may or may not have different chemical or physical properties than the original compound and may or may not have improved biological and/or chemical activity. For example, the analog may be more hydrophilic or it may have altered reactivity as compared to the parent compound. The analog may mimic the chemical and/or biologically activity of the parent compound (i.e., it may have similar or identical activity), or, in some cases, may have increased or decreased activity.

In one aspect, the derivative or analog compound has a chemical structure of Formula I wherein $R_1$ is —PSe(OH)$_2$ and (i) $R_2$-$R_6$ (i.e., $R_2$, $R_3$, $R_4$, $R_5$, and $R_6$) are —PO(OH)$_2$ or (ii) $R_2$-$R_6$ are independently —PO(OH)$_2$, —PS(OH)$_2$, —PSe(OH)$_2$, —AsO$_3$, or PO(OH)$_2$NO, but not all are —PO(OH)$_2$. In certain aspects, $R_2$ is —PSe(OH)$_2$, and $R_1$ and $R_3$-$R_6$ are —PO(OH)$_2$. In further aspects, $R_4$ is —PSe(OH)$_2$, and $R_1$-$R_3$ and $R_5$-$R_6$ are —PO(OH)$_2$. In still further aspects, $R_5$ is —PSe(OH)$_2$, and $R_1$-$R_4$ and $R_6$ are —PO(OH)$_2$. In certain aspects, $R_1$-$R_4$ are —PSe(OH)$_2$ and $R_5$-$R_6$ are —PO(OH)$_2$. In certain aspects, one or more of the —PO(OH)$_2$ groups is further modified to a —PO(OH)$_2$NO. The NO group can be covalently or non-covalently bound to the analog. In a further aspect, the compound is a pharmacologically effective salt or derivative of these compounds.

In certain aspects, the derivative or analog compound has a chemical structure of Formula I where $R_1$ is —PS(OH)$_2$ and $R_2$-$R_6$ are —PO(OH)$_2$. In further aspects, $R_2$ is —PS(OH)$_2$ and $R_1$ and $R_3$-$R_6$ are —PO(OH)$_2$. In still further aspects, $R_4$ is —PS(OH)$_2$ and $R_1$-$R_3$ and $R_5$-$R_6$ are —PO(OH)$_2$. In certain aspects, $R_1$, $R_5$, and $R_3$ are —PS(OH)$_2$, and $R_2$ and $R_4$-$R_6$ are —PO(OH)$_2$. In further aspects, $R_5$ is —PS(OH)$_2$ and $R_1$-$R_4$ and $R_6$ are —PO(OH)$_2$. In still further aspects, $R_1$-$R_4$ are —PS(OH)$_2$ and $R_5$-$R_6$ are —PO(OH)$_2$. In certain aspects the analog is an inhibitor of exotoxin cleavage. In certain aspects, the compounds are pharmacologically effective salt or derivative of these compounds.

In a further aspect, the derivative or analog compound has a chemical structure of Formula I where $R_1$-$R_6$ independently are —PO(OH)$_2$ or —PO(OH)2NO (NO associated covalently or ionically with —PO(OH)$_2$), whereby at least one of $R_1$-$R_6$ is NO associated with —PO(OH)$_2$, or a pharmacologically effective salt or derivative thereof.

In certain embodiments an inositol analog has a chemical structure of Formula I where $R_1$, $R_2$, $R_3$, $R_4$, $R_5$, and $R_6$ are independently —PS(OH)$_2$, —PSe(OH)$_2$, —AsO$_3$, or —PO(OH)NO. In certain aspects, $R_1$, $R_2$, $R_3$, $R_4$, $R_5$, and $R_6$ are —PS(OH)$_2$. In certain aspects, $R_1$, $R_2$, $R_3$, $R_4$, $R_5$, and $R_6$ are —PSe(OH)$_2$. In certain aspects, $R_1$, $R_2$, $R_3$, $R_4$, $R_5$, and $R_6$ are —AsO$_3$. In certain aspects, $R_1$, $R_2$, $R_3$, $R_4$, $R_5$, and $R_6$ are —PO(OH)$_2$NO. In certain aspects, $R_1$, $R_2$, and 1, 2, 3, or 4 of $R_3$, $R_4$, $R_5$, and $R_6$ are —PS(OH)$_2$, —PSe(OH)$_2$, —AsO$_3$, or —PO(OH)$_2$NO. In further aspects $R_1$, $R_4$, and 1, 2, 3, or 4 of $R_2$, $R_3$, $R_5$, and $R_6$ are —PS(OH)$_2$, —PSe(OH)$_2$, —AsO$_3$, or —PO(OH)NO. In still further aspects, $R_1$, $R_5$, and 1, 2, 3, or 4 of $R_2$, $R_3$, $R_4$, and $R_6$ are —PS(OH)$_2$, —PSe(OH)$_2$, —AsO$_3$, or —PO(OH)NO. In certain aspects, $R_1$, $R_6$, and 1, 2, 3, or 4 of $R_2$, $R_3$, $R_4$, and $R_5$ are —PS(OH)$_2$, —PSe(OH)$_2$, —AsO$_3$, or —PO(OH)NO. In certain embodiments the inositol analog is a myo-inositol analog.

IV. Pharmaceutical Preparations

Pharmaceutical compositions of the present invention comprise an effective amount of an S-nitrosylating agent and/or an inositol phosphate or analog thereof dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition that contains at least one S-nitrosylating agent and/or an inositol phosphate or analog thereof. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical compositions of the invention may comprise different types of carriers depending on whether it is to be administered in solid, liquid, or aerosol form, and whether it needs to be sterile for such routes of administration, e.g., injection. The present invention can be administered orally or rectally (e.g., to facilitate delivery to the gastrointestinal tract), but may also be administered by any other local or systemic route (e.g., intratracheally, intranasally, subcutaneously, mucosally, inhalation (e.g., aerosol inhalation), injection, infusion, continuous infusion, localized perfusion bathing target cells directly, via a catheter, via a lavage, or by other method or any combination of the foregoing as would be known to one of ordinary skill in the art) (see, e.g., Remington's Pharmaceutical Sciences, 18th Ed. Mack Printing Company, 1990).

The actual dosage amount of a composition administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject. In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof. Liposomal delivery is useful when the agents are gaseous, volative or need stabilization.

In certain embodiments, the compositions of the present invention are prepared for administration by such routes as oral ingestion. In these embodiments, the solid composition may comprise, for example, solutions, suspensions, emulsions, tablets, pills, capsules (e.g., hard or soft shelled gelatin capsules), delayed release capsules, sustained release formulations, buccal compositions, troches, elixirs, suspensions, syrups, wafers, or combinations thereof. Oral compositions may be incorporated directly with food. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations suitable for other modes of administration include suppositories. Suppositories are solid dosage forms of various weights and shapes, usually medicated, for insertion into the rectum. After insertion, suppositories soften, melt or dissolve in the cavity. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level.

The compositions of the present invention may be specially formulated for release after administration. More particularly, the compositions may be designed for release or synthesis in the stomach, the small intestine, the ileum, the jejunum, the duodenum, the large intestine, the cecum, the ascending colon, the transverse colon, the descending colon, the sigmoid colon or the rectum.

V. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A. Materials and Methods

Materials. Materials were obtained from Sigma-Aldrich Chemical Company (St Louis, Mo.) or Invitrogen (Carlsbad, Calif.) unless otherwise stated and r-InsP$_7$ ((rad)-1(3)-PP-(2,3A,5,6)\nsP$_5$) and m-InsP$_7$ (D-myo-5-PP-(1,2,3,4,6)InsP$_5$ was obtained from Dr. Glenn Prestwich (University of Utah, Utah)).

Generation, Treatment and Testing of Native and Recombinant *C. Difficile* Toxins. Purification of TcdA and TcdB from toxigenic *C. difficile* strain 10463 was performed and tested for cytotoxicity as described (Savidge et al., *Gastroenterology* 125:413-20 (2003)). Toxin purity was assessed by SDS-PAGE, confirming molecular masses for TcdA and TcdB as 308 kDa and 270 kDa, respectively. The EZ-Link® Sulfo-NHS-LC-Biotinylation Kit (Pierce) was used to biotinylate toxin on primary amide-groups without altering its biological activity or interfering with cysteine-thiol groups required for activity or S-nitrosylation. N-Hydroxysuccinimide (NHS) ester-activated biotins react efficiently with primary amino groups (—NH$_2$) at pH 7.4 to form stable amide bonds. One mg of TcdA or TcdB was dissolved in 0.85 ml of phosphate-buffered saline (PBS). The Sulfo-NHS-LC-Biotin solution (150 µl) was then added to the protein solution and incubated on ice for two hours. Remaining biotin reagent was then removed by using a desalting column (Zeba™ Desalt Spin Column). Biotinylated toxin concentrations were measured by the Bradford method (Bio-Rad, Hercules, Calif.) and purity assessed by gel electrophoresis, confirming the expected molecular mass of 308 kDa for TcdA and 270 kDa for TcdB. For S-nitrosylation of *C. difficile* toxins, 100 µg of purified TcdA or TcdB in 20 mM Hepes, 5 mM EDTA, pH 7.2 was S-nitrosylated with 100 µM GSNO for 10-30 min and then separated to remove excess GSNO using Vivaspin 500 (100,000 mw cut-off filters; Sartorius biotech) or acetone precipitation. S-nitrosylation reactions were also run in the presence of increasing concentrations of InsP$_6$ or r-InsP$_7$ ((rac1)-1(3)-PP-(2,3,4,5,6)InsP5). *C. difficile* toxins with an inactivated cysteine protease domain were prepared by incubation with 100 µM N-ethylmalemeide and InsP$_6$ for 30 min before removing excess inhibitor using Vivaspin 500 filters.

Full-length, bioactive recombinant TcdA and TcdB have been successfully cloned and expressed in a *B. megaterium* system, achieving a toxin expression level of 10 mg/L (Yang et al. *BMC Microbiol* 8:192-98 (2008); Sun et al. *Microb Pathog* 46:298-305 (2009)). To test S-nitrosylation effects on intracellular autocleavage efficiency in cells, several recombinant TcdB proteins were generated, including the point mutations Cys698Ser (catalytic cysteine), His653Ala (catalytic histidine), Glu743Ala (glutamic acid forming part of the S-nitrosylation motif), and glucosyltransferase (GT)-domain substrate binding residues (Trp102Ala and Asp288Asn) that essentially abolish TcdB toxicity (but do not alter affect cellular internalization or $InsP_6$ induced self-cleavage)(Sun et al. *Microb Pathog* 46:298-305 (2009)). The GT-mutant recombinant toxin was named aTcdB and contains a C-terminus His-tag to facilitate toxin recovery as described using an anti-His tag monoclonal antibody or HisPur™ cobalt resin (Thermo Scientific) (Yang et al. *BMC Microbiol* 8:192-98 (2008); Sun et al. *Microb Pathog* 46:298-305 (2009)).

In Vitro and BioCore Toxin Cleavage Assays. Autocleavage of 1 µg TcdA and TcdB holotoxins, and recombinant native and mutant TcdB was performed in 25 µl 20 mM Tris-HCl, 150 mM NaCl (pH 7.4) with and without $InsP_6$, GSNO, GSH, or DTT for 10 min to overnight at 37° C. as described (Egerer et al., *J Biol Chem* 282: 25314-21 (2007)). For nitroso-thiocyanobenzoic acid (NTCB)-induced toxin cleavage reactions, 1 µg of toxin was incubated with a 5-fold molar excess of NTCB in 1M Glycine-Tris buffer (pH 9.0) for 2 hrs to overnight at 37° C. as previously described (Tang et al., *Analyt Biochem* 334:48-61 (2004)). Cleavage reactions were stopped with SDS-PAGE loading buffer and boiling at 96° C. for 5 min. Samples were then run under reducing conditions on 4-20% gradient gels and cleavage products were stained with GelcodeBlue™ (Pierce) for 1 hr and cleared in water overnight. Cleavage fragments were then identified by mass spectrometry. $AC_{50}$ and $IC_{50}$ concentrations were calculated by measuring the relative absorbance of cleavage fragments relative to intact toxin using a LiCor Odyssey infrared scanner (λ=680 nm). Cleavage was plotted against ligand concentration using four-parameter logistic curve fitting on SigmaPlot 11.0 software. Real time BiaCore-X toxin cleavage assays were performed essentially as described (Lupardus et al., *Science* 322: 265-68 (2008)), with the following modifications: unconjugated or biotinylated toxin was bound to a captured anti-toxin (A1H3) or anti-biotin (BN34) antibodies on CM5 sensor chips as recommended by the manufacturer. Flow rates for toxin cleavage assays were run at 5-10 µl $min^{-1}$ in degassed HBS-EP buffer (BIACORE). Analysis was performed using BIAsimulations software (BIACORE).

[$^3$H] Inositol Hexakisphosphate Binding Assays. ($^3$H-$InsP_6$, 10-30 Ci/mmol) NET-1023 was from Perkin Elmer (Waltham, Mass.). The binding buffer (BB) in the assays was 25 mM Hepes (pH 7.2), containing 100 mM KCl and 1 mM EDTA. The $^3$H-$InsP_6$ stock (in BB) was cleared at 18,000×g for 3 min at 4° C before use in assays. The binding reactions in protein LoBind tubes (Eppendorf, Westbury, N.Y.) included 2 µg of purified TcdA and various concentrations of $^3$H $InsP_6$. The binding reactions were incubated for 10 min with gentle shake at 4° C. and then cold 30% PEG8000 (in BB) was added to final concentration of 20% and the incubation was continued without shaking for 10 min. TcdA was precipitated at 18,000×g for 20 min at 4° C. The supernatant was thoroughly removed, and the pellet was resuspended with 200 µl of 2% SDS into 5 ml of ScintiVerse II (Fisher Scientific, Pittsburg, Pa.) and counted in a LS6500 scintillation counter (Beckman, Fullerton Calif.). Nonspecific background at 1 mM of cold $InsP_6$ was subtracted and B-Max and Kd values were analyzed by nonlinear and Scatchard analyses with GraphPad Prism 5 software. The effect of GSNO on $InsP_6$ binding was assayed by preincubating TcdA in the dark at RT for 30 minutes with and without 100 µM GSNO. UV treatment (302 nm) was for 10 min at 9000 µW/$cm^2$.

Circular Dichroism (CD) Spectroscopy. CD spectra were recorded on an Aviv 62 spectropolarimeter in the wavelength range of 190-260 nm, with a bandwidth of 1.0 nm and scan step of 0.5 nm using a 0.1-cm path length in a 1-cm quartz cell at 22° C. The protein concentration was in the range of 50-200 µg/ml. In each case, at least five spectra were accumulated, smoothed, averaged, and corrected for the contribution of solutes.

Cell culture. Human-derived colonic adenocarcinoma Caco-2 cells were obtained from the American Tissue Culture Collection. Cells were cultured at 37° C. in a 5% $CO_2$ atmosphere in Dulbecco's Modified Eagle Media (DMEM) with 10% fetal calf serum, 50 U/ml penicillin and 50 µg/ml streptomycin.

Toxin-Exposure of Cell Lines. Caco-2 cells transiently-transfected with pCMV6-eNOS (seq identical to NM_000603, which is incorporated herein by reference) or control vector pCMV6 were seeded in 6 well or 96 well tissue culture plates at a concentration of $5 \times 10^4$ cells per well, in 100 µl of media. Amaxa-Nucleofector based electroporations were performed according to the manufacturer's instructions (Lonza Walkersville Inc. Walkersville, Md.) and typically resulted in 50% transfection rates. After 48 hrs, cells were treated to facilitate calcium influx and 12 hours later intoxicated with TcdA or TcdB (dose-range of 0.4-to-40 nM) for 3-15 min and cells were then washed 3× with fresh media. For short term experiments testing Rac1 glucosylation levels, cells were intoxicated for 10-120 min and cell lysates were probed with Rac23A8 (total Rac1) and Rac102 (non-glucosylated) antibodies. For acute cellular autocleavage assays, transfected cells were intoxicated with recombinant aTcdB (20 nM) for 3 min before harvesting cell lysates. For MTT assays, cells were cultured for a minimum of 48 hrs after toxin exposure. Cells were washed with PBS and 90 µl of fresh media without phenol red and 10 µl of MTT (5 mg/ml) added for 3 hours at 37° C. The insoluble formazan salt is dissolved by adding 100 µl of 20% (w/v) SDS in 10 mM HCl, followed by overnight incubation at 37° C. Absorbance of the converted dye is measured at 550 nm. In test cultures where toxin was retrieved for SNO analysis and mass spectrometry, transfected cells were seeded in 75 cm² tissue culture flasks for 48 hours and were intoxicated with 1-10 µg of toxin or biotinylated toxin for 10 min. Cells were then processed for precipitation of toxin using streptavin-beads or immunoprecipitation with antibody (rabbit anti-nitrocysteine (SNO) specific antibody (Sigma; N5411)). Recombinant His-tagged toxins were enriched as described (Yang et al. *BMC Microbiol* 8:192-98 (2008)). Alternatively, TcdB intoxicated cells were processed for SNO-immunoblotting or biotin-switch assay. Additional control experiments included 1-10 mM membrane-permeable GSH-ethyl ester (GSH-EHH) to elevate intracellular GSH in eNOS-transfected cells prior to intoxication. Intracellular GSHis generated by the action of cytoplasmic esterases. Inhibiting eNOS activity in Caco-2 cells was achieved using $N^G$-nitro-L-arginine methyl ester (L-NAME; 100 µM). iNOS-deficient mice (B6.128S2-Nos2$^{tm1Mrl}$ N12) were obtained from Taconic and intraperitoneal macrophages were harvested a described (Ng et al., *Gastroenterology* Apr. 13 (2010); Sun et al. *Microb Pathog* 46:298-305 (2009)).

Cell Free Rac1 Glucosvlation Assay. Glucosyltransferase activity of TcdA and TcdA-SNO was measured by their ability to glucosylate Rho GTPase Rac1 in a cell-free assay. Caco-2 cell pellets were resuspended in glucosylation buffer (50 mM HEPES, pH 7.5, 100 mM KCl, 1 mM $MnCl_2$ and 2 mM $MgCl_2$) and lysed with a syringe (25G, 40 passes through the needle). After centrifugation (167,000×g, 3 min), the supernatant was used as a post-nuclear cell lysate. To perform the glucosylation assay, the cell lysates were incubated with TcdA or TcdA-SNO (final concentration of the toxins was 5 µg/ml) at 37° C. for 30 min. The reaction was terminated by heating at 100° C. for 5 min in SDS-sample buffer. To measure Rac1 glucosylation levels, lysates were separated on a 4-20% gradient SDS-PAGE gel and transferred onto a nitrocellulose membrane. An antibody that specifically recognizes the non-glucosylated form of Rac1 (clone 102, BD Bioscience) was used for detection.

TcdA-Exposure of Mouse Ileal Loops. Cd-1 mice (10 week old males; Charles River Labs) were fasted overnight. Ileal loops were ligated in anesthetized animals via laparotomy and injected with 0.15 ml of purified TcdA, TcdA-SNO or TcdA-NEM (10 µg) or buffer as described (Savidge et al., *Gastroenterology* 125:413-20 (2003); Oiu et al., *Gastroenterology* 111: 409-18 (1996)). Test animals were additionally pretreated with GSNO, $InsP_6$ or GSNO+$InsP_6$ (0.1 ml; 10 mg/kg+$InsP_6$1 mM) for 15 min prior to inoculation of TcdA. Four hrs after TcdA administration, mice were euthanized and fluid secretion was determined as the loop weight (100 mg)-to-length (cm) ratio. Full thickness loops were frozen in liquid nitrogen or fixed in 10% formalin in PBS (pH 7.2) for 24 hours and embedded in paraffin using routine procedures. Histological severity of enteritis was evaluated by assessing (1) epithelial cell necrosis, (2) hemorrhagic congestion and edema of the mucosa, and (3) neutrophil margination and tissue infiltration (Savidge et al., *Gastroenterology* 125:413-20 (2003); Oiu et al., *Gastroenterology* 111: 409-18 (1996)).

Murine *C. Difficile* Infection Model. A conventional mouse model of antibiotic-induced *C. difficile* infection that closely resembles the spectrum of disease manifest in humans was used as described (Chen et al., *Gastroenterology* 135:1984-92 (2008)). Disease severity varies from fulminant with typical histopathologic features of *C. difficile* infection, to minimal diarrhea depending on challenge dose. 12 week-old C57BL/6 mice were pre-treated for three days with a mixture of antibiotics shown to disrupt the intestinal microflora (Chen et al., *Gastroenterology* 135:1984-92 (2008)). After two days, mice were injected with clindamycin and were challenged intragastrically with $10^6$ *C. difficile* VPI 10463 vegetative cells the following day. Therapeutic efficacy of GSNO and $InsP_6$ alone or in combination were performed by oral gavage of GSNO (10 mg/kg/day)+$InsP_6$ (0.25 mg/Kg/day). Oral administration of vancomycin (50 mg/kg/day) was used as a positive control. In addition, GSNO combinations were administered intracecally via catheter using 7 day ALZET mini-osmotic pumps (Durect Corp, Cupertino, Calif.) surgically implanted 3 days before *C. difficile* challenge as described (Savidge et al., *Gastroenterology* 132:1344-58 (2007)).

Myeloperoxidase Assay. Neutrophil myeloperoxidase (MPO) activity is an indicator of tissue inflammation. Intestinal segments (100-250 mg) were homogenized in 1 ml HTAB buffer and centrifuged at 20,000×g for 10 min at 4° C. Pellets were resuspended in 1 ml HTAB buffer containing 1% hexadecyltrimethlammonium to negate pseudoperoxidase activity. MPO activity was measured in supernatants following 3 cycles of sonication, freezing and thawing. After centrifugation at 40,000×g for 15 min at 4° C., supernatants (10 µl) were mixed with 90 µl of potassium phosphate buffer containing 0.167 mg/ml O-dianiside dihydrochloride and 0.0005% hydrogen peroxide. Activity was measured every 2 minutes for 20 minutes at 450 nm.

Quantitative Cytokine mRNA Measurements. Total RNA was extracted from cells or frozen tissues, treated with 1 U DNAse I and reversed transcribed (Gene Amp RNA-PCR Kit). Real-time rtPCR reactions were run with SYBR Green PCR Master-Mix for 40 cycles on a Chromo4 detector (Bio-Rad Ltd) (94° C. for 2 min; 94° C. for 1 min; 60° C. for 1 min; 72QC for 1min; repeat step 2-to-4 for 40 cycles; 72° C. for 10 min). Primer sets were for human IL-8: (Forward 5'-GCCGTGGCTCTCTTGGC-3' SEQ ID NO:2; Reverse 5'-GCACTCCTTGGCAAAACTGC-3' SEQ ID NO:3); murine TNFα (Forward 5'-ATGAGCACA-GAAAGCATGATC-3' SEQ ID NO:4, Reverse 5'-TACAG-GCTTG TCACTCGAATT-3' SEQ ID NO:5); murine IL-1γ (Forward 5'-TTGACGGACCCCAAA AGATG-3' SEQ ID NO:6, Reverse 5'-AGAAGGTGCTCATGTCCTCA-3' SEQ ID NO:7). Samples were normalized against commercial GAPDH or 18S rRNA primers and probes (Applied Biosystems) and relative expression levels were calculated as previously described (Savidge et al., *Gastroenterology* 132: 1344-58 (2007)).

Hg—Coupled Photolysis/Chemiluminescence Determination of Tissue GSNO Concentrations. Briefly, tissue samples were homogenized in PBS (pH 7.4), 0.1 mM EDTA, 0.1 mM DTPA and processed for tissue GSNO as described (Hausladen et al., *Proc Natl Acad Sci USA*. 104: 2157-62 (2007)). Samples were introduced into a photolysis unit (a borosilicate glass coil illuminated with a 200 W mercury vapor lamp for photolytic cleavage of bound NO) via an HPLC capillary pump. NO is then carried in a helium gas stream to a chemiluminescence analyzer (Thermo Electron Corp. TEA 610).

Biotin-Switch Assay. The biotin-switch assay was performed away from direct sunlight essentially as described (Jaffrey et al., *Sci STKE* 12:86 (2001)) with the following modifications. Cell lysates were incubated at 0.8 mg of protein per ml in HENS buffer (200 mM Hepes, 1 mM EDTA, 0.1 mM neocuproine, 2.5% SDS, pH 7.7) containing 20 mM S-methylmethane thiosulfonate (MMTS) for blocking of free thiols at 50° C. for 40 min. Excess MMTS was then removed by precipitating the proteins with four volumes of cold 100% acetone for one hour at −20° C. After centrifugation at 4000×g for 30 min, the pellet was washed 3 times with 70% acetone and re-suspended in 0.5 ml of 50 mM Hepes, 1% SDS, 1 uM CuCl. Reduction and biotinylation of the SNO's was done by adding 0.5 ml of Reducing and Labeling reagent (S-Nitrosylated Protein Detection Assay Kit, Cayman Chemical Co., Ann Arbor, Mich.) and incubating at room temperature for one hour. The proteins were then precipitated with 100% acetone and resuspended in 0.5 ml of 25 mM Hepes, 1 mM EDTA, 1% SDS. For Streptavidin pull-down, 250 µl of the suspension was diluted with 750 µl of neutralization buffer (25 mM Hepes, 100 mM NaCl, 1 mM EDTA, 0.5% Triton X-100, pH 7.7). This solution was tumbled overnight at 4° C. with 30 µl of streptavidin agarose beads, which had been pre-washed with neutralization buffer. The beads were pelleted at 200×g for 30 s, washed with neutralization buffer containing 600 mM NaCl, pelleted and resuspended in 5×SDS-PAGE sample loading buffer. Supernatants of boiled samples were separated on 10% SDS-PAGE and immunoblotted for TcdB.

Cysteine-Saturation Fluorescence Assay for 2-D Gel Separation and Analyses of the S-Nitrosoproteome. After processing tissue samples to the ascorbate step as described above, the biotin-switch label was substituted with use of a BODIPY-Fl-maleimide fluorescent conjugate (Life Technologies, Inc., Carlsbad, Calif.). Amino acid analysis was first used to determine the cysteine content of the protein sample. Protein (400 µg) was then labeled with BODIPY® FL N-(2-aminoethyl)maleimide at a 1:75 ratio cysteine:BodipyFL maleimide. The reaction buffer was 7M urea, 2M thiourea, 2% CHAPS, 50 mM Tris pH 7.5. Incubation time for labeling was 2 hrs at RT. To quench the reaction, 10× molar excess β-mercaptoethanol (BodipyFL: βME) was added and incubated for 30 min at room temperature. The final reaction volume (400 µl) used for isoelectric focusing contained 200 µg labeled protein+0.5% IPG buffer pH3-10 (GE Healthcare), and was loaded onto a 11 cm pH3-10 IPG strip (GE Healthcare) in duplicate and proteins were focused using the following protocol: (1) 50V×11 hrs (hydration of strip); (2) 250V×1 hr; (3) 500V×1 hr; (4) 1.000V×1 hr; (5) 8,000V×2 hr (steps 2-5 are gradient increases in voltage); and (6) 8,000V×48,000 V/hr. Prior to running the second dimension, IPG strips were equilibrated in 6M Urea, 2% SDS, 50 mM Tris, pH 8.8, 20% glycerol×30 min RT and applied to wells of 8-16% Tris-glycine-SDS gels. Gels were run at 150V×2.25 hr at 4° C., fixed for 1 hr in 10% methanol, 7% acetic acid and washed overnight in 10% ethanol. Finally, gels were imaged on a ProXpress 2D Proteomic Imaging System (Perkin Elmer; excitation λ=480/40 nm & emission λ=535/50 nm). It was demonstrated that this covalent derivatization method using an uncharged thio-reactive dye: (i) exhibits good specificity for reduced cysteine residues, (ii) has minimal effects on the pi of proteins allowing separation by isoelectric focusing, and (iii) can provide precise quantification due to saturation labeling (Pretzer, et al., *Analyt. Biochem.* 374:250-62 (2008)). Furthermore, this sensitive thiol-labeling method is amenable for in-gel digestion for identification by peptide mass fingering.

S-nitrosocysteine (SNO) in Gel and Western Blotting. Purified toxin-SNO samples were run on 4-20% gradient SDS polyacrylamide gels under non-reducing conditions. Gels were then incubated in 50% isopropanol 5% acetic acid for 15 min with gentle shaking, washed in ultrapure water (1 mM EDTA, 0.1 mM neocuproine) for 15 min, before incubating with anti-nitrosocysteine (SNO) antibody (1:200; Sigma) overnight. Gels were then washed 3× with PBS+ 0.1% tween-20. Alternatively, toxin was transferred onto nitrocellulose membrane. SNO-toxin was visualized following incubation with an anti-rabbit IR800 antibody (1:5000) using infrared imaging on an Odyssey imager (Li-Cor Biosciences).

SNO-Immunofluorescence. Frozen tissue sections of murine ileal loops or colonic mucosa from control and ulcerative colitis patients (n=4/group), were fixed in FACS™ lysing solution (BD Biosciences) for 20 minutes and blocked with rat serum (1:20 in PBS) for 15 min at room temperature. Samples were then incubated with AF®647 conjugated anti-S-Nitroso-Cysteine (SNO) polyclonal rabbit Abs (1:200 in PBS) at room temperature for one hour. Rabbit conjugated IgG was included as a control. Each staining step was followed by six washes with PBS. Samples were then mounted in SlowFade® Gold antifade reagent with DAPI. Confocal microscopy was performed with a Zeiss LSM510 META laser scanning confocal microscope (Carl Zeiss, Thornwood, N.Y.). DAPI stain was visualized with an excitation of 351-364 nm and emission at 385-470 nm (UV laser). The AF®647 staining was detected with an excitation wavelength of 633 nm and an emission wavelength longer than 650 nm (red helium/neon laser). Specificity was demonstrated by a loss of immunofluorescence following pretreatment of sections with 0.1% mercuric chloride as previously described (Gow et al., *J Biol Chem* 277: 9637-40 (2002)).

*C. difficile* Patients and Stool Cytotoxicity (ICT) Assay. Coded stool samples from patients with antibiotic-associated diarrhea were investigated for *C. difficile* infection. Eight unformed stool specimens tested positive for TcdA by western blot (A1H3) and for stool cytotoxicity by ICT assay (He et al., *J Microbiol Methods* 78:97-100 (2009)). For the ICT cytotoxicity assay, stool samples were diluted in PBS (50-fold) and filtered through a 0.2 μm membrane. Samples were mixed with A1H3 (2 μg/ml final conc.) and mRG1 cells ($2\times10^4$/well) before adding to E-plates as described (He et al., *J Microbiol Methods* 78:97-100 (2009)). A control set of wells included neutralizing antibody (1:1000 of goat anti-TcdA from TechLab, Inc) to specifically block TcdA activity. Cell indexes (CIs) of wells were monitored and a positive sample was defined as a CI value (in the absence of anti-sera) equal or less than 50% of that in the presence of anti-sera. TcdA S-nitrosylation was investigated by anti-nitrosocysteine (SNO) antibody immunoprecipitation and detection with A1H3 antibody as described.

Mass Spectrometry. Two complementary strategies were used to conduct more detailed mapping of the site(s) of S-nitrosylation in TcdA and TcdB. In the first, toxins were subjected to limited proteinase K digestion, followed by the biotin-switch assay resulting in cleavage of full length toxin into smaller biotinylated fragments. Mass spectrometry was then used to identify which fragments were mostly associated with S-nitrosylation following strepatividin pulldown. Alternatively, gel samples of SNO-labeled or autocleaved toxin fragments were cut into 1 mm size pieces or smaller and placed into separate 0.5 mL polypropylene tubes. 100 μl of 50 mM ammonium bicarbonate buffer was added to each tube and the samples were then incubated at 37° C. for 30 min. After incubation, the buffer was removed and 100 μl of water was added to each tube. The samples were then incubated again at 37° C. for 30 min. After incubation, the water was removed and 100 μl of acetonitrile was added to each tube to dehydrate the gel pieces. The samples were vortexed, and after 5 min the acetonitrile was removed. 100 μl of acetonitrile was again added to each of the sample tubes, vortexed, and acetonitrile removed after 5 minutes. The samples were then placed in a speedvac for 45 minutes to remove any excess solvent. A 25 mM ammonium bicarbonate solution was prepared at pH 8.0. To a 20 μg vial of lyophilized trypsin (Promega Corp.) was added 2 mL of 25 mM ammonium bicarbonate. The trypsin solution was then vortexed. Trypsin solution was added to each sample tube in an amount (approximately 10 μL) to just cover the dried gel. The samples were then incubated at 37° C. for 6 hrs. After digestion, 1 μL of sample solution was spotted directly onto a MALDI target plate and allowed to dry. 1 μL of alpha-cyano-4-hydroxycinnamic acid (Aldrich Chemical Co.) matrix solution (50:50 acetonitrile/water at 5 mg/mL) was then applied on the sample spot and allowed to dry. The dried MALDI spot was blown with compressed air (Decon Laboratories, Inc.) before inserting into the mass spectrometer.

Matrix-Assisted Laser Desorption Ionization Time-of-Flight Mass Spectrometry (MALDI TOF-MS) was used to analyze the samples and determine protein identification. Data were acquired with an Applied Biosystems 4800 MALDI TOF/TOF Proteomics Analyzer. Applied Biosystems software package included 4000 Series Explorer (v. 3.6 RC1) with Oracle Database Schema Version (v. 3.19.0), Data Version (3.80.0) to acquire both MS and MS/MS spectral data. The instrument was operated in positive ion reflectron mode, mass range was 850-3000 Da, and the focus mass was set at 1700 Da. For MS data, 2000-4000 laser shots were acquired and averaged from each sample spot. Automatic external calibration was performed using a peptide mixture with reference masses 904.468, 1296.685, 1570.677, and 2465.199. Following MALDI MS analysis, MALDI MS/MS was performed on several (5-10) abundant ions from each sample spot. A 1kV positive ion MS/MS method was used to acquire data under post-source decay (PSD) conditions. The instrument precursor selection window was +/−3 Da. For MS/MS data, 2000 laser shots were acquired and averaged from each sample spot. Automatic external calibration was performed using reference fragment masses 175.120, 480.257, 684.347, 1056.475, and 1441.635 (from precursor mass 1570.700). Applied Biosystems GPS Explorer™ (v. 3.6) software was used in conjunction with MASCOT to search the respective protein database using both MS and MS/MS spectral data for protein identification. Protein match probabilities were determined using expectation values and/or MASCOT protein scores. MS peak filtering included the following parameters: mass range 800 Da to 4000 Da, minimum S/N filter=10, mass exclusion list tolerance=0.5 Da, and mass exclusion list (for some trypsin and keratin-containing compounds) included masses 842.51, 870.45, 1045.56, 1179.60, 1277.71, 1475.79, and 2211.1. For MS/MS peak filtering, the minimum S/N filter=10.

For protein identification, eukaryotic and bacterial taxonomy was searched in the NCBI database. Other parameters included the following: selecting the enzyme as trypsin; maximum missed cleavages=1; fixed modifications included BODIPY Fl-maleimide for 2-D gel analyses only; variable modifications included oxidation (M); precursor tolerance was set at 0.2 Da; MS/MS fragment tolerance was set at 0.3 Da; mass=monoisotopic; and peptide charges were only considered as +1. The significance of a protein match, based on both the peptide mass fingerprint (PMF) in the first MS and the MS/MS data from several precursor ions, is based on expectation values; each protein match is accompanied by an expectation value. The expectation value is the number of matches with equal or better scores that are expected to occur by chance alone. The default significance threshold is p<0.05, so an expectation value of 0.05 is considered to be on this threshold. A more stringent threshold of $10^{-3}$ was used for protein identification; the lower the expectation value, the more significant the score.

Ligand Docking Studies to the Toxin Cysteine Protease Domain. There are four toxin cysteine protease crystal structures available (3EEB and 3FZY of RTXvc, 3H06 of TcdA and 3PA8 of TcdB). These structures show that the catalytic residues, the β-flap and larger helices are conserved. The RTXvc 3FZY structure includes the uncut N-terminus substrate. The crystal structures of RTXvc (3FZY), TcdB (3PA8) and the TcdB glucosyltransferase domain (2BVL) were combined to generate a combined model of the glucosyltransferase and cysteine protease domain in TcdB. An N-terminus elongated TcdA model was also generated from the uncut RTXvc 3FZY structure and imposed on the 3H06 TcdA structure using methods described (Navaratnarajah et al. *Nat Struct Mol. Biol.* 18:128-34 (2011)). For ligand docking studies to the toxin crystal structures, the properties and structures of the inositolphosphate family members were evaluated and the most favorable AutoDock scores were measured and the estimated binding energy was compared to that of $InsP_6$ as described (Chen et al. *Bioorg Med Chem* 16:7225-33 (2008)).

Statistical Analysis. Results are presented as mean values+S.E.M. Statistical significance was determined using t-test, Mann-Whitney U test on Ranks and ANOVA on ranks on SigmaStat software, n=3 unless otherwise stated; P<0.05 was considered statistically significant.

B. Results

*C. difficile* Toxins are Molecular Targets of S-Nitrosylation. Using a well characterized *C. difficile* toxigenic disease model (Oiu et al., *Gastroenterology* 111: 409-18 (1996); Ng et al., *Gastroenterology* 139(2):542-52 (2010)), there was significant pathophysiology when purified TcdA was injected into ileal-loops in Cd-1 mice. TcdA induced significant epithelial cell damage, neutrophil infiltration and edema of the intestinal mucosa, fluid secretion into the intestinal lumen and accumulation of proinflammatory gene transcripts for iNOS, TNF-α and IL-1γ (FIG. 1A-1B).

Figure 1D:
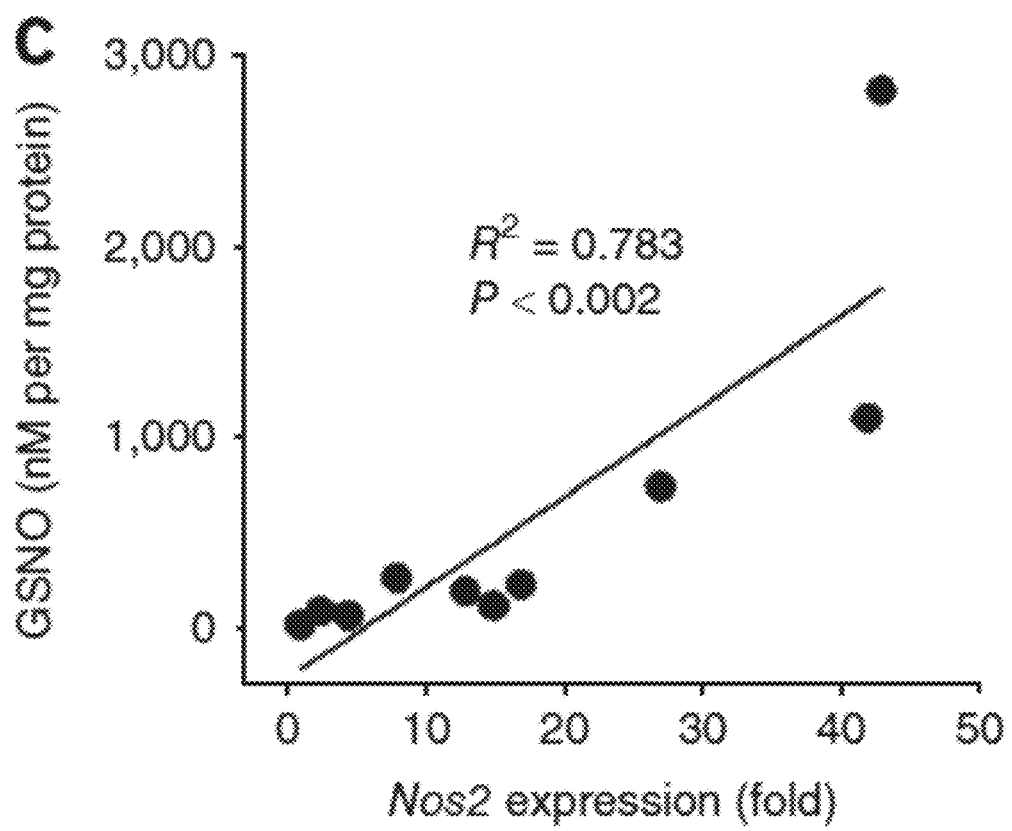
Figure 1E:
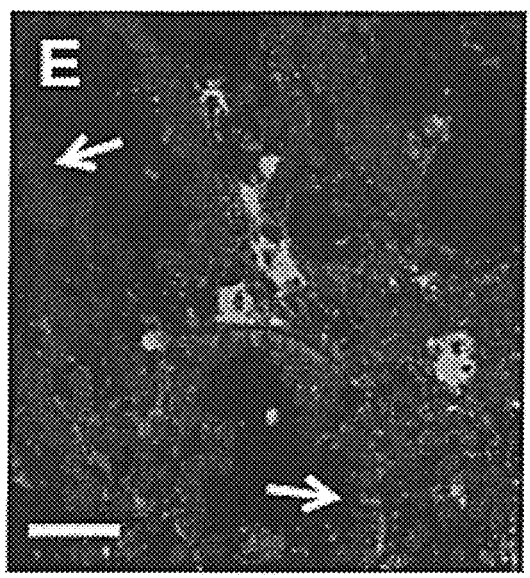
Figure 1F:
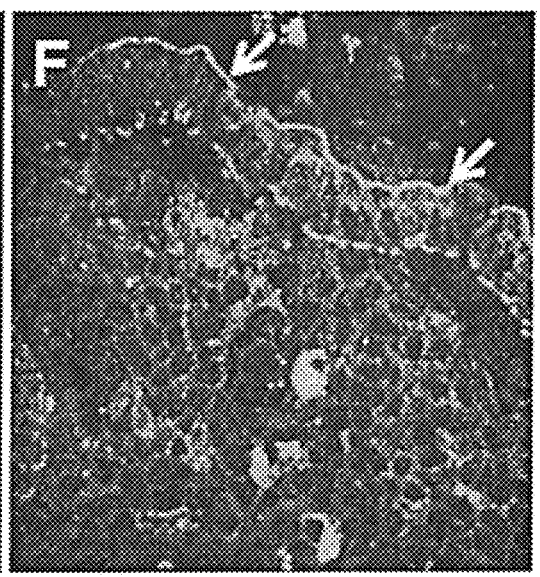

To identify S-nitrosylation signals that may regulate disease severity to *C. difficile* toxins, tissue concentrations of S-nitrosoglutathione (GSNO), a small endogenous S-nitrosothiol that constitutes the main source of NO bioactivity in the respiratory (Que et al., *Science* 308:1618-21 (2005)) and gastrointestinal tract (Savidge et al., *Gastroenterology* 132: 1344-58 (2007)) where it protects against inflammatory disease were measured. Using $HgCl_2$-coupled photolysis-chemiluminescence (Que et al., *Science* 308:1618-21 (2005); Hausladen et al., *Proc Natl Acad Sci USA*. 104: 2157-62 (2007)), a 12.1-fold increase in tissue GSNO concentrations was demonstrated following TcdA-intoxication (84+29.1 versus 1020+475 nM/mg protein, respectively; p<0.05; +SD), which correlated with elevated iNOS expression levels (FIG. 1D). The effects of GSNO are mediated primarily by SNO-proteins (Benharefa, Nat Rev Mol Cell Bio. 10:721-31 (2009)). Immunofluorescence labeling of SNO-proteins in tissue sections using an anti-nitrosocysteine antibody demonstrated large increases within TcdA-exposed intestinal mucosa, and in particular, apical brush border epithelial staining of intoxicated, but not normal, samples. A similar SNO-protein tissue distribution was evident in biopsies from patients with active colitis, which suggests that epithelial SNO accumulation is also of pathophysiological relevance in the human colon during inflammatory conditions (FIGS. 1E-1F).

Figure 1G:
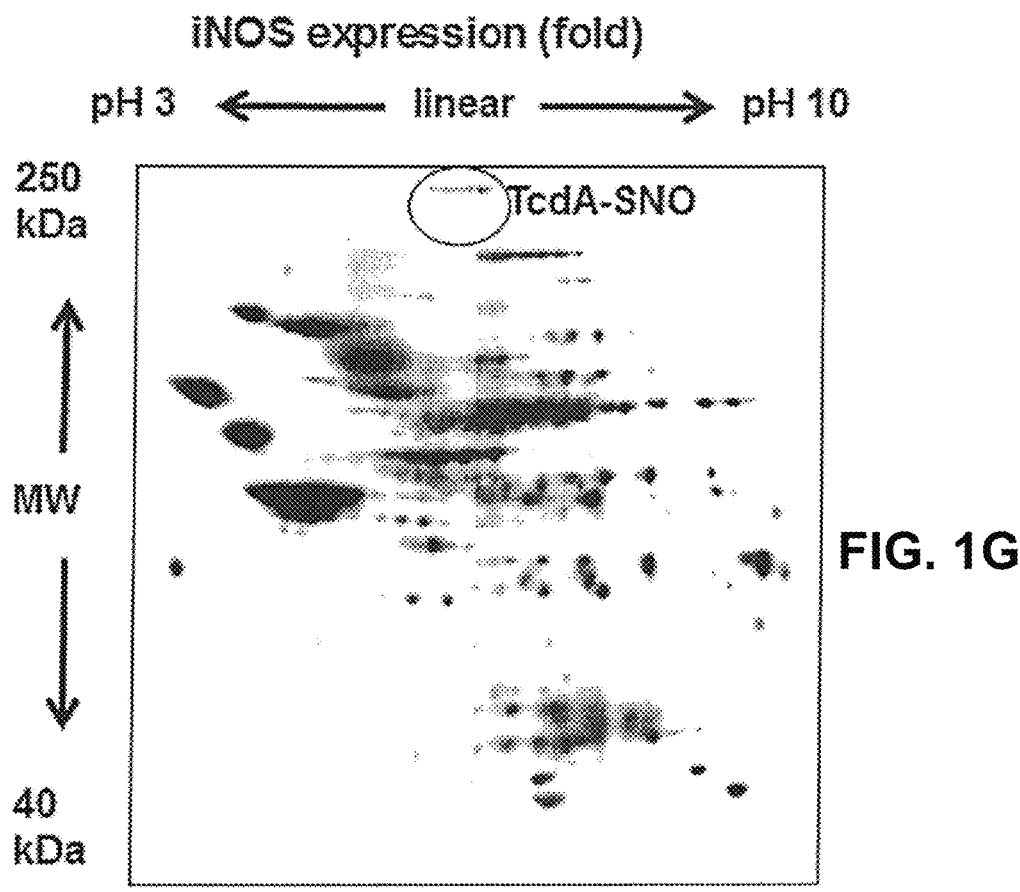
Figure 1H:
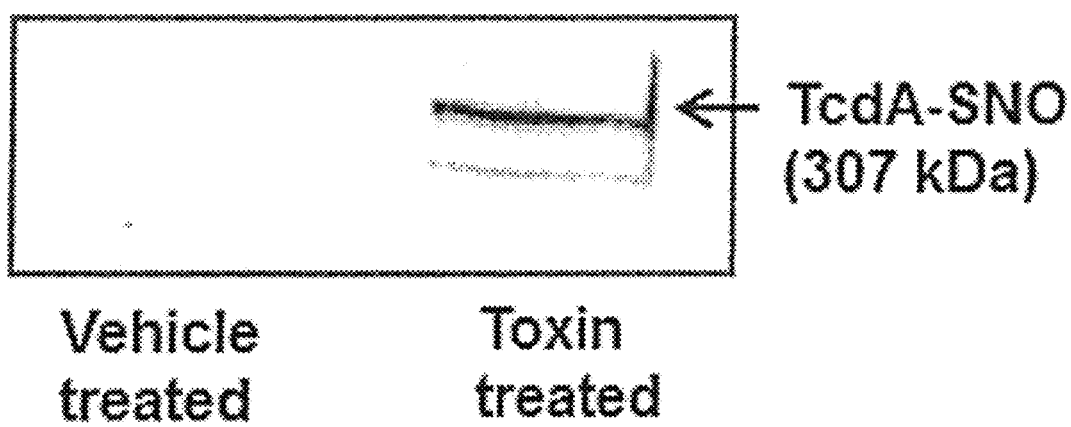

The toxin-induced S-nitrosoproteome was characterized using a cysteine saturation fluorescence assay (Pretzer et al., *Analyt. Biochem.* 374:250-62 (2008)). Cysteine saturation labeling and mass fingering of up regulated SNO-proteins identified several species that are known targets of S-nitrosylation, including hemoglobin, cytoskeletal, heat-shock and various cell signaling proteins (FIG. 1G). *C. difficile* infection is therefore associated with increases in tissue S-nitrosylation that reflect toxin-induced pro-inflammatory responses. Cysteine saturation labeling also consistently identified TcdA as a molecular target of S-nitrosylation in inflamed tissues (FIG. 1G), which was confirmed by a biotin-switch assay (Jaffrey et al., *Sci STKE* 12:86 (2001)) that specifically labels Cys-NO adducts (FIG. 1H).

S-nitrosylation Inhibits *C. difficile* Toxin Virulence. Because there is no precedent for in situ S-nitrosylation of foreign proteins in host tissues, an in vitro model was established to examine the potential significance of toxin S-nitrosylation. To recapitulate the epithelial protein-SNO accumulation observed during *C. difficile* infection, human Caco-2 colonocytes were transfected with a calcium-inducible endothelial nitric oxide synthase construct (pCMV6-eNOS) to transiently raise cellular SNO levels prior to intoxication (Gow et al., *J Biol Chem* 277:9637-40 (2002)) (FIGS. 2A-2C).

Figures 2E, 2F:
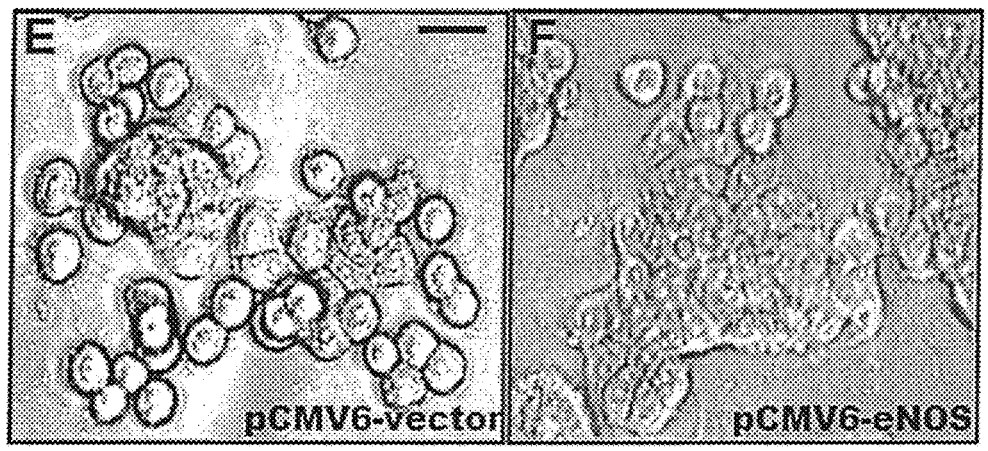
Figure 2G:
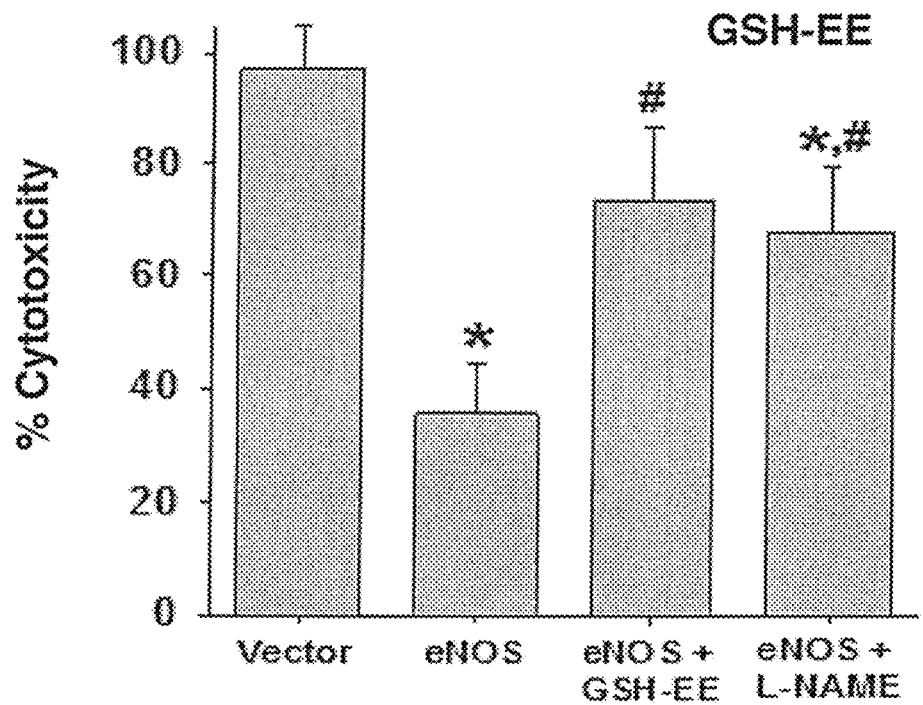
Figure 2H:
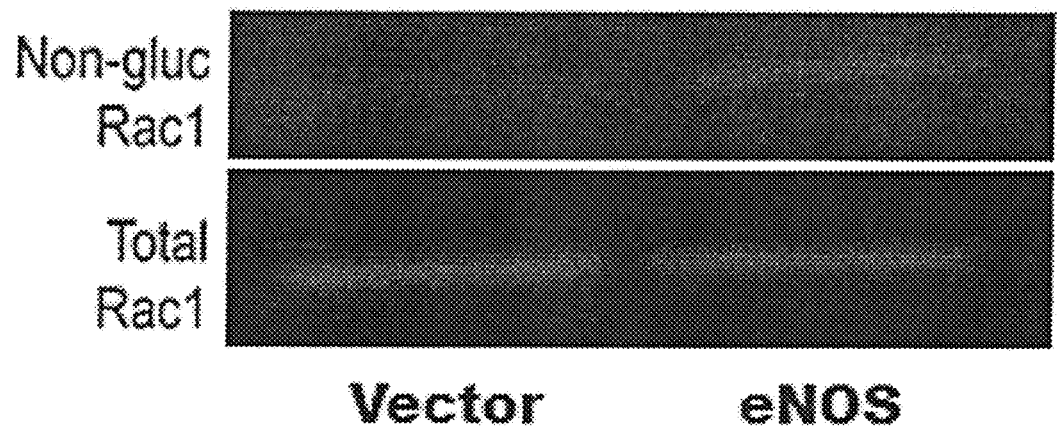
Figure 2I:
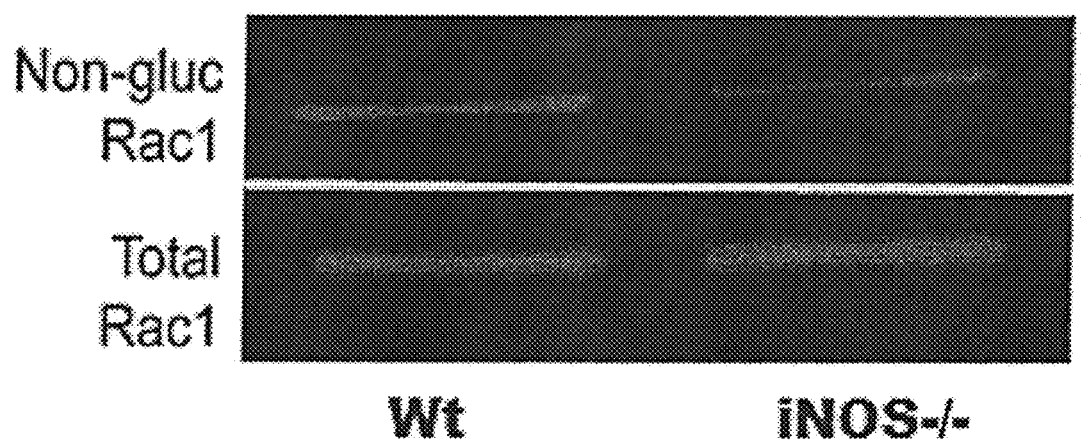

Biotin-switch assay and anti-SNO immunoblotting confirmed the in vivo findings that toxin recovered from cellular lysates was preferentially S-nitrosylated in pCMV6-eNOS transfected Caco-2 cells, and S-nitrosylation was abolished by addition of the membrane-permeable denitrosylating agent, GSH-ethyl ester (Gow et al., *J Biol Chem* 277:9637-40 (2002)) (FIG. 2D). Toxin-induced cell rounding and viability assays demonstrated that elevated SNO in pCMV6-eNOS transfected Caco-2 cells conferred significant protection against intoxication (FIGS. 2E-2G). Moreover, toxin UDP-glucosylation of RhoGTPases (Popoff et al., *Biochim Biophys Acta*. 88:797-812 (2009)) was significantly reduced in eNOS-transfected cells, indicting an early SNO-based protective mechanism (FIG. 2H). This protective effect was significantly attenuated by GSH-ethyl ester and by inhibition of eNOS enzymatic activity using N(G)-nitro-L-arginine methyl ester (L-NAME) (FIG. 2G). In support of the premise that toxin S-nitrosylation is a physiological inhibitory mechanism of the *C. difficile* toxins, murine iNOS-deficient peritoneal macrophages were also more susceptible to intoxication when compared with wild type cells which express abundant SNO (Kim et al., *Science* 2005 310:1966-70 (2005)) (FIG. 2I).

Figure 3A:
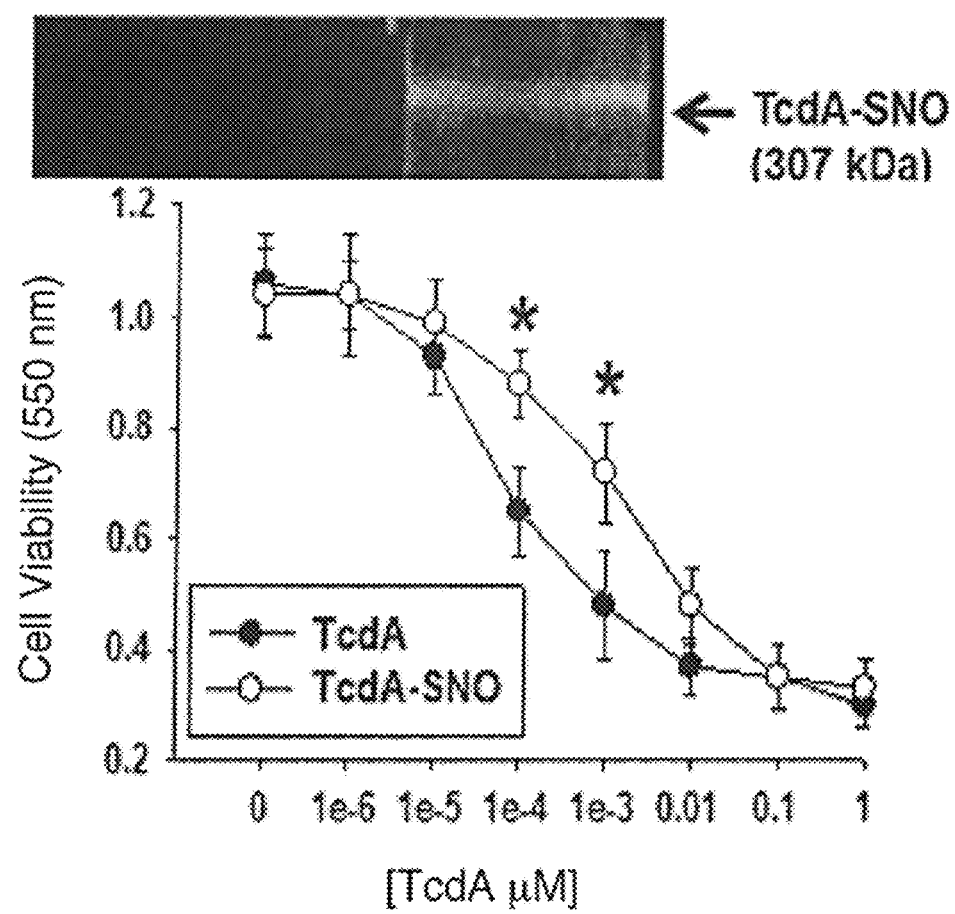
Figure 3B:
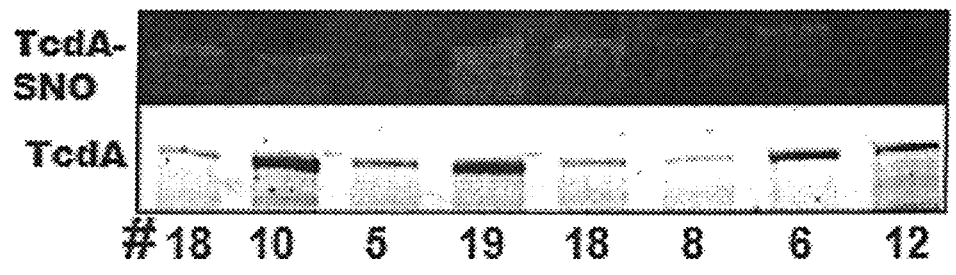
Figures 3C, 3D:
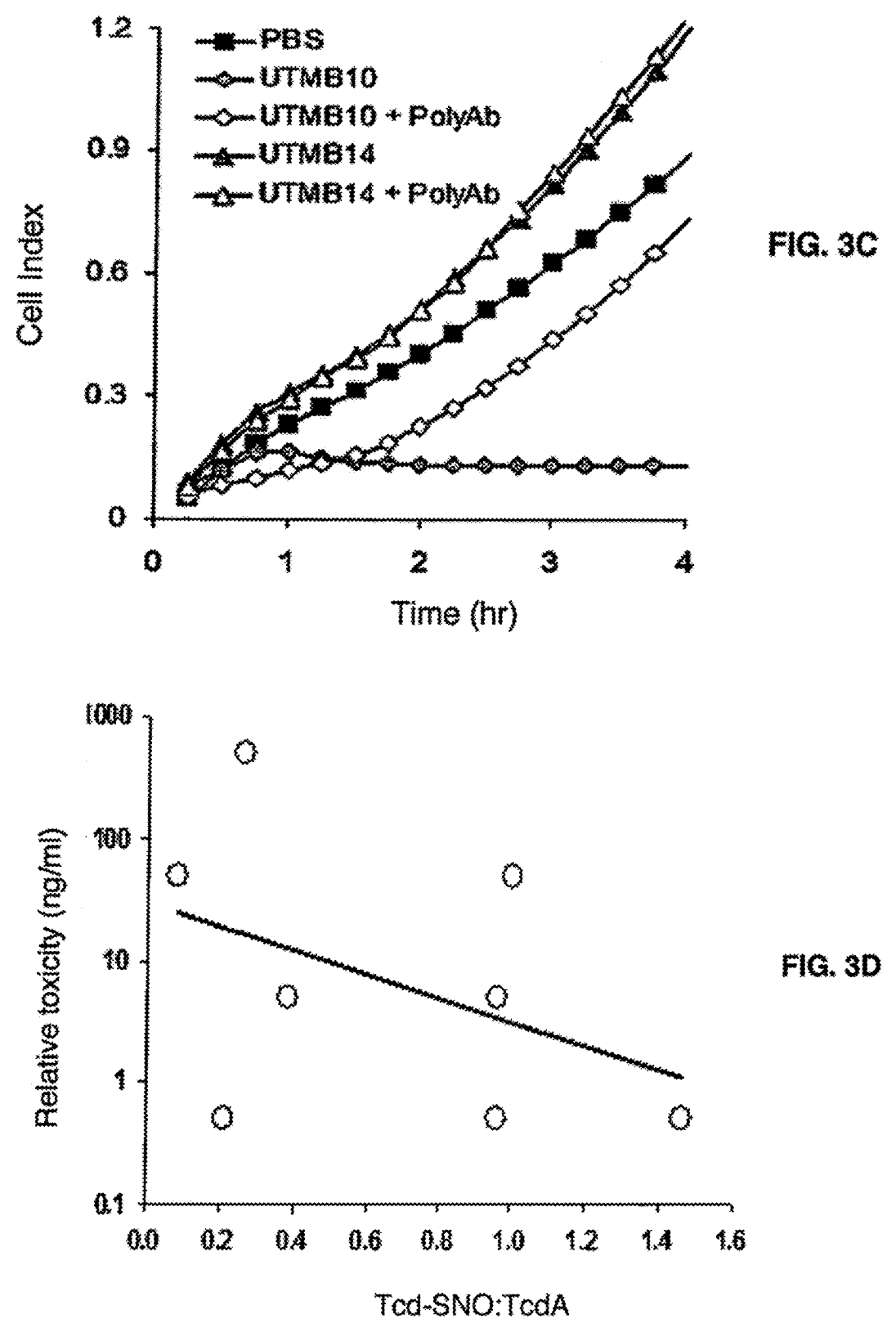

To confirm that these cytoprotective effects were directly linked to S-nitrosylation of the exotoxin, the S-nitrosylated toxin was assessed in pure form. Purified TcdA was treated with GSNO and formation of SNO was confirmed by biotin-switch assay (FIG. 3A). In vitro studies showed that the S-nitrosylated toxin (toxin-SNO) was significantly less cytotoxic when compared with unmodified toxin (FIG. 3A), and the protective effects of S-nitrosylation were abolished by glutathione (GSH) or dithiothreitol (DTT), which denitrosylated the toxin (FIG. 2D). TcdA-SNO was also significantly less cytotoxic in vivo in the murine ileal loop model (FIG. 1C). Pathophysiological relevance of these data was further suggested by finding S-nitrosylated toxin in stool samples from patients with *C. difficile* infection, and by the inverse relationship between levels of toxin-SNO and stool cytotoxicity (He et al., *J Microbiol Methods* 78:97-100 (2009)) (FIG. 3B-3D). Thus, toxin S-nitrosylation is both physiologically and functionally significant.

Figure 4A:
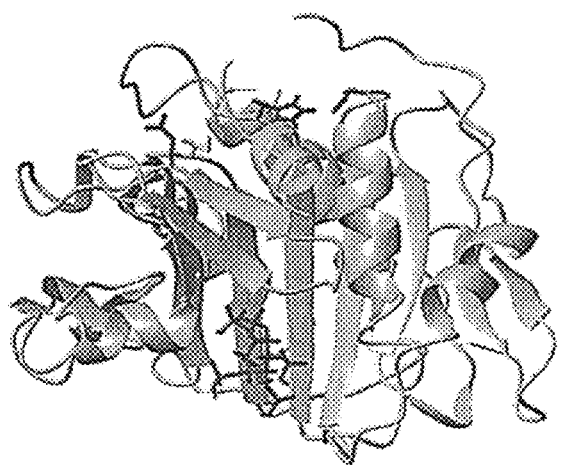
FIGS. 4A-4H. Toxin S-nitrosylation is allosterically regulated by $InsP_6$ and $InsP_7$.
Figure 4C:
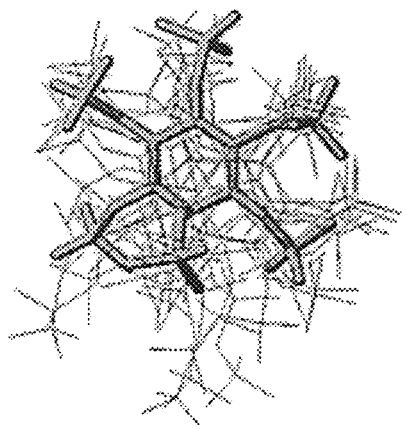
Figure 4B:
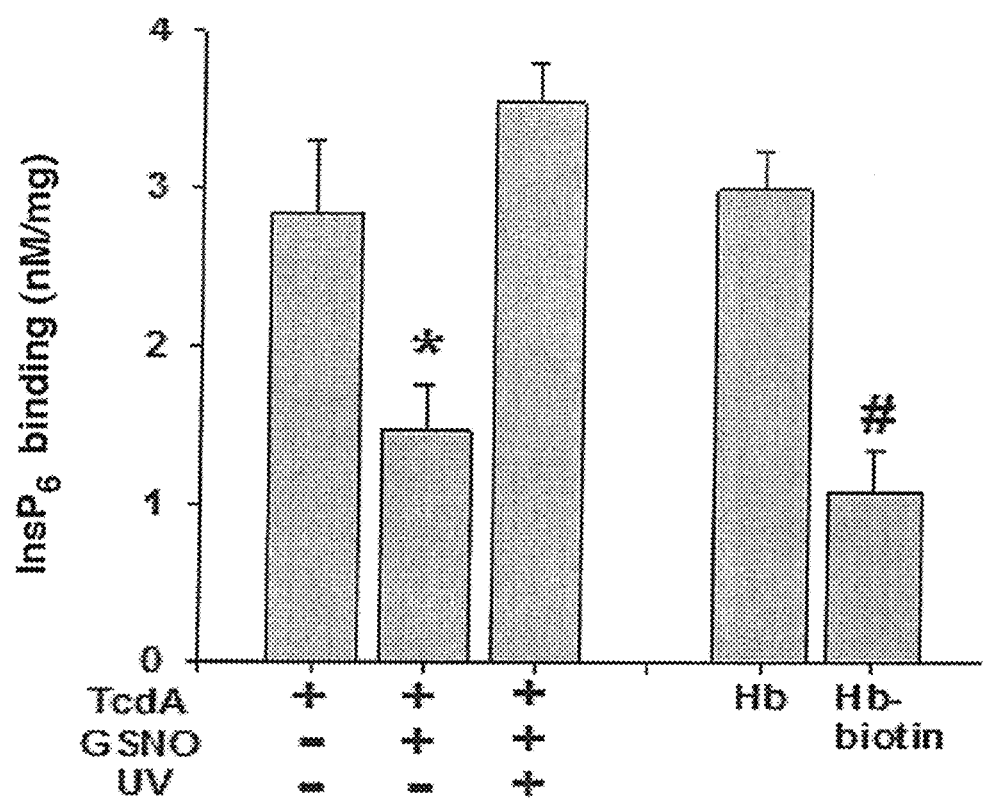
Figure 4D:
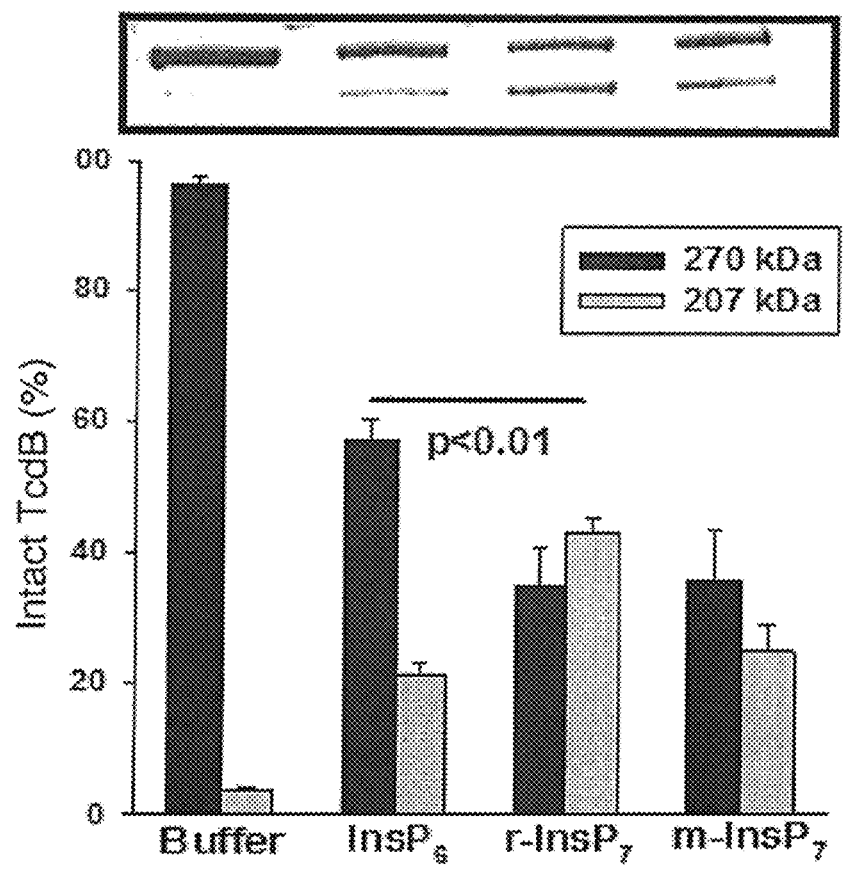

Allosteric Inositolphosphate Potentiates S-Nitrosvlation of the Toxin Cysteine Protease Active Site. The S-nitrosylated residues responsible for inactivation of *C. difficile* toxins was investigated. Cysteine residues targeted by S-nitrosylation often conform to an exposed acid-base consensus motif (Marino et al., *J Mol Biol* 395: 844-59 (2010)). There are seven cysteine residues in TcdA and nine in TcdB, with four being conserved between the two toxins. Because cysteine proteases may be regulated by S-nitrosylation of the cysteine-histidine catalytic dyad[17], whether the toxin cysteine protease domain is a preferred target for posttranslational modification by GSNO was examined. High resolution crystal structures of the TcdA (Pruitt et al., *J Biol Chem* 284:21934-40 (2009)) and TcdB (Puri et al., *Chem. Biol.* 17:1201-11 (2010)) cysteine protease domains, and the closely aligned *Vibrio cholerae* RTX toxin (Lupardus et al., *Science* 322:265-68 (2008); Prochazkova et al., *J Biol Chem* 284:26557-68 (2009)), show a well-defined catalytic cleft that is separated from a positively charged $InsP_6$ binding pocket abutting a β-hairpin fold (β-flap) (FIG. 4A). Data confirmed that $InsP_6$ binds to *C. difficile* TcdA holotoxin, yielding an equilibrium binding affinity constant ($K_d$) of 62.6+7.0 nM, which is in close agreement with the $AC_{so}$ concentration for the TcdA cysteine protease domain (Pruitt et al., *J Biol Chem* 284: 21934-40 (2009)) (FIG. 4B). In silico determination of the binding energies of the various inositolphosphate family members to the allosteric binding pocket in TcdA and TcdB demonstrated good docking scores for $InsP_6$, and even better values for $InsP_7$, a member of the higher inositolpyrophosphates (Chakraborty et al., *Cell* 143: 897-910 (2010)) (FIG. 4C). The prevailing binding affinity of $InsP_7$ was confirmed experimentally by demonstrating significantly greater toxin autocleavage activity for $InsP_7$ than for $InsP_6$ (FIG. 4D). Moreover, the enhanced cleavage activity of $InsP_7$ was not due to toxin autophosphorylation as a result of the high energy pyrophosphate bond. Thus, the phylogenically ancient inositolpyrophosphates may play an important role in regulating *C. difficile* toxin virulence, perhaps via privileged access to the toxin at the plasma membrane (Chakraborty et al., *Cell* 143:897-910 (2010)).

Figure 4E:
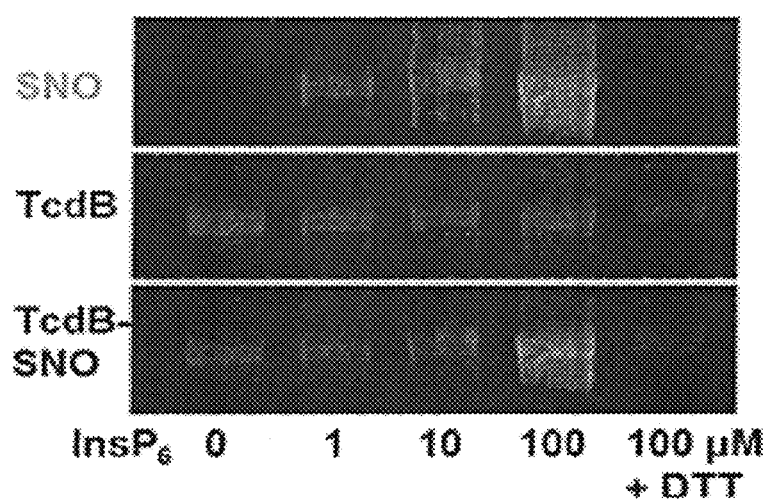
Figure 4F:
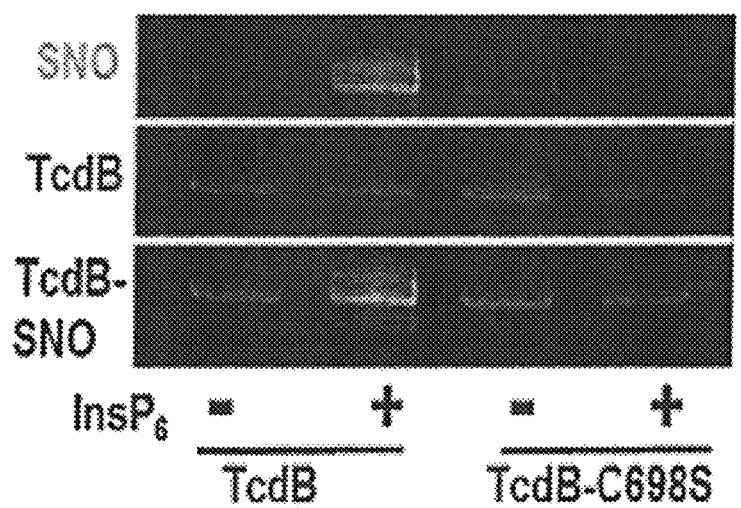
Figure 4G:
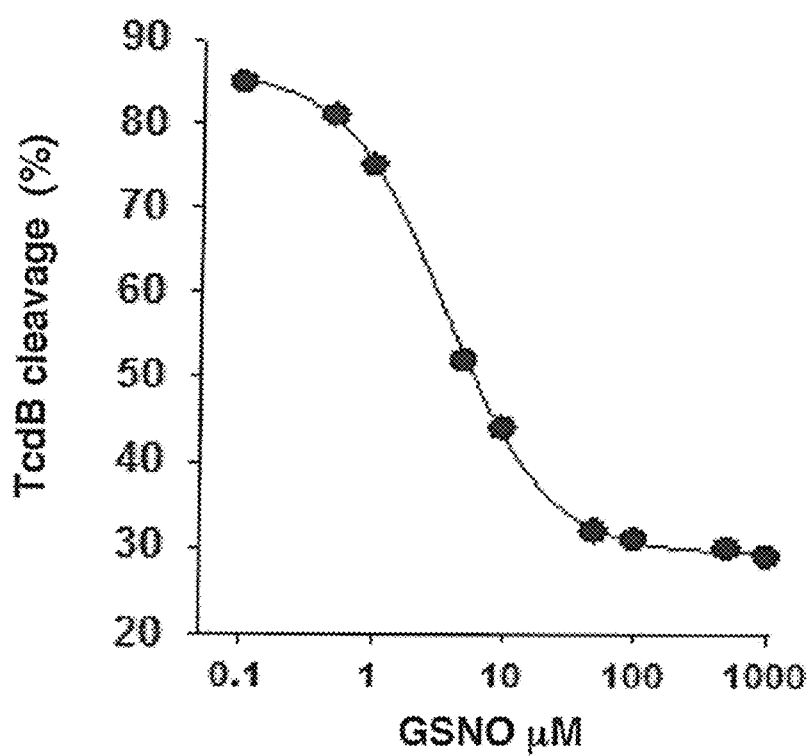
Figure 4H:
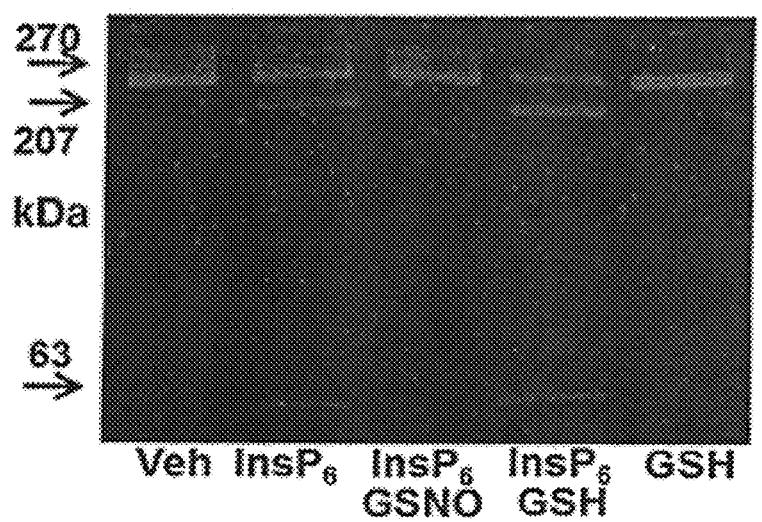

Because of the heterotropic nature of the inositolphosphate interaction with the toxin through specific binding to the cysteine protease domain (Prochazkova et al., *J Biol Chem* 283:23656-64 (2008); Popoff et al., *Biochim Biophys Acta*. 88:797-812 (2009); Pruitt et al., *J Biol Chem* 284: 21934-40 (2009)), the enzymatically active inositolphosphate bound form appears to be the preferential target for S-nitrosylation. Multiple lines of experimental evidence supported this view: (i) $InsP_6$ and $InsP_7$ potentiated S-nitrosylation of TcdB by GSNO (FIG. 4E), and this effect was abolished by site-directed mutation of Cys698 to alanine in TcdB (FIG. 4F); (ii) Standard in vitro (FIGS. 4G-4H) and realtime toxin cleavage assays demonstrated that GSNO rapidly inhibits $InsP_6$ induced toxin self-cleavage with an $IC_{50}$ of 12.9+4.2 µM for TcdB (analogous to inhibition by N-ethylmaleimide and novel peptide analogues that inhibit TcdB virulence via covalent modification of the catalytic cysteine(Puri et al., *Chem. Biol.* 17:1201-11 (2010)), only GSNO is an endogenous species), (iii) cysteine-specific cyanylation of *C. difficile* toxins using nitro-thiocyanobenzoic acid (NTCB)-based cleavage assays (Tang et al., *Analyt Biochem* 334: 48-61 (2004)) identified TcdA Cys700 and TcdB Cys698 as preferential cleavage fragments following $InsP_6$ treatment. GSNO inhibited this cleavage reaction demonstrating that these cysteine residues are modified by S-nitrosylation and are, as such, not amenable to cyanylation; (iv) S-nitrosylated cysteine protease domain peptide fragments were preferentially identified by mass spectrometry after $InsP_6$ and GSNO co-treatment; (v) Significant SNO inhibition of TcdB-autocleavage is evident in eNOS-Caco-2 cells, demonstrating that S-nitrosylation prevents the intracellular release of the toxin N-terminus effector domain, which is dependent on inositolphosphate binding; (vi) GSNO treatment of toxin significantly inhibited $InsP_6$ binding to the cysteine protease domain, an effect that was reversed by UV-cleavage of the SNO bond (FIG. 4B). This 'linkage' indicates that S-nitrosylation of the active site cysteine residue regulates communication with the $InsP_6$ binding pocket, possibly by disordering the (β-flap (Lupardus et al., *Science* 322: 265-268 (2008); Pruitt et al., *J Biol Chem* 284: 21934-40 (2009); Prochazkova et al., *J Biol Chem* 284:26557-68 (2009); Kreimeyer et al., *Naunyn Schmiedebergs Arc Pharmacol.* 2010 Nov. 3). (vii) QSNO did not inhibit toxin binding to Caco-2 cells or alter glucosyltransferase activity in cell lysates. Taken together, these data indicate that inositol phosphate cofactors enable GSNO to specifically inhibit *C. difficile* toxin via S-nitrosylation of the cysteine protease catalytic residue, and that S-nitrosylation of the active site Cys has the added effect of displacing the allosteric activator. Thus, GSNO inhibits the toxin by a novel dual orthosteric and allosteric mechanism of action. Notably, several ions ($Ca^{2+}$, $Mg^{2+}$, $H^+$) and $O_2$/redox have been shown to allosterically regulate protein S-nitrosylation (Hess, et al., *Nature Rev* 6: 150-166 (2005)), and NO binding to Cys93 in hemoglobin, which provides vasodilatory activity upon deoxygenation (Hess, et al., *Nature Rev* 6: 150-166 (2005); M W et al., *Trends Mol Med* 15:391-404 (2009)), is a prototypic example of allosteric regulation, with predicted consequences for $InsP_6$ binding (McMahon et al., *J Biol Chem* 275:16738-45 (2000)). Taken together, these data raise the idea that crosstalk between NO signaling and the inositolphosphate family may be more widespread.

Figure 5A:
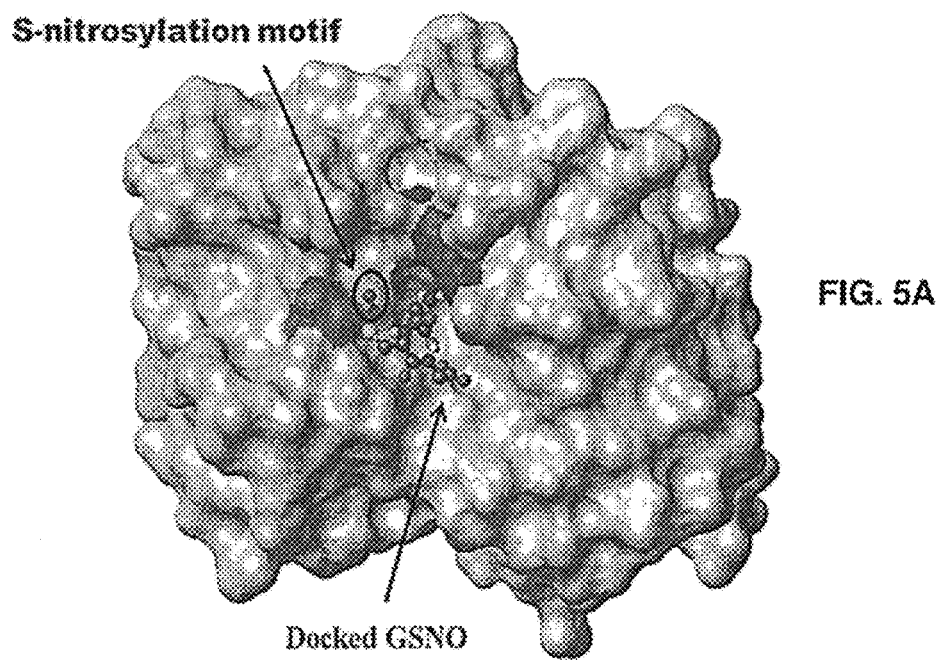
FIGS. 5A-5G. A novel microbial S-nitrosylation-catalytic motif.
Figure 5B:
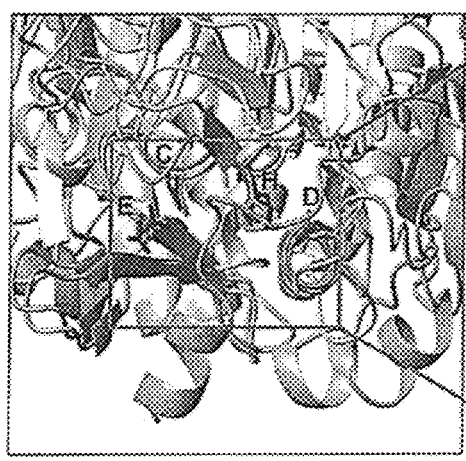
Figure 5D:
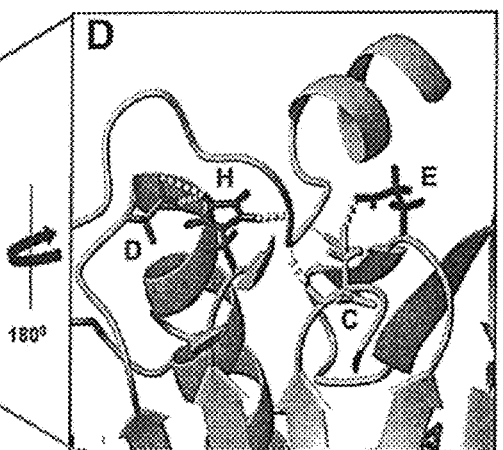
Figure 5C:
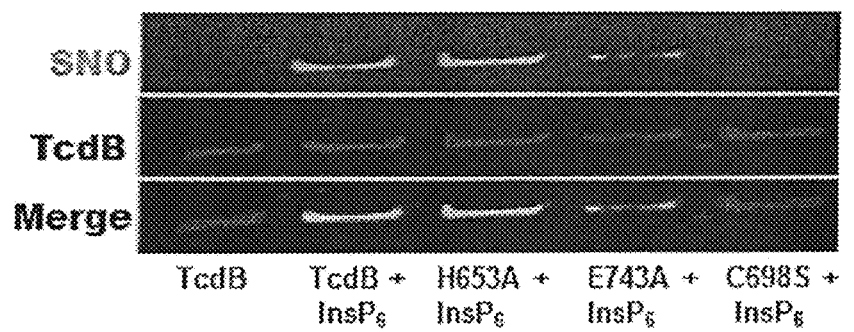
Figure 5E:
Figure 5F:
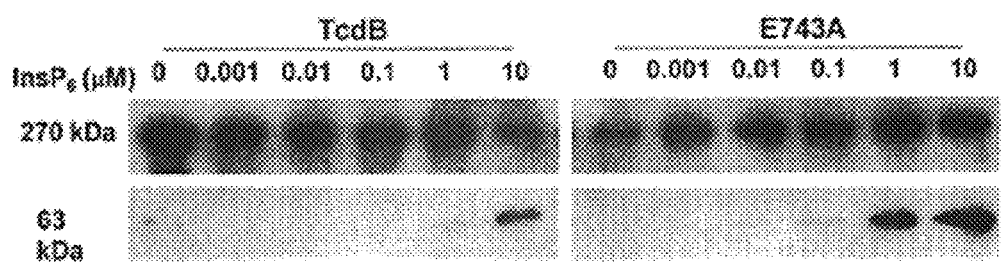
Figure 5G:
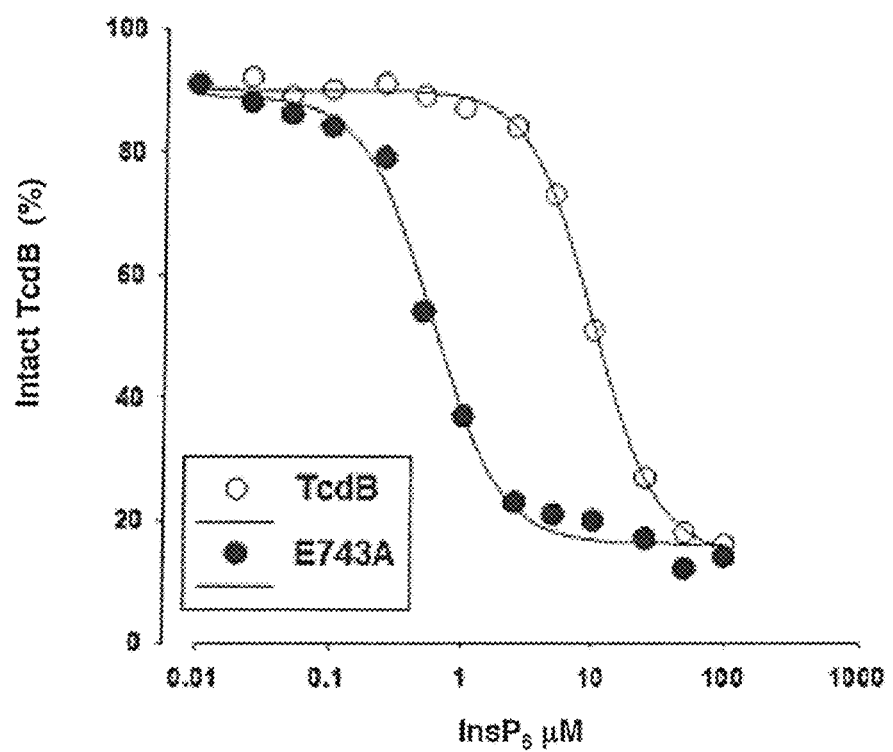

A Novel Toxin S-Nitrosylation-Catalytic Motif. The premise that *C. difficile* toxins are regulated by S-nitrosylation is strengthened further by in silico docking studies of GSNO to the toxin cysteine protease crystal structure, which predicts an excellent alignment of the S—NO bond with the active site cysteine which forms part of an exposed acid-base S-nitrosylation consensus motif (FIG. 5A). This dual S-nitrosylation-catalytic motif is structurally conserved amongst microbial cysteine proteases, with glutamic acid (Glu) and histidine (His) residues juxtaposing the catalytic Cys700 in TcdA, Cys698 in TcdB, Cys3568 in *V. cholera* RTX toxin (Prochazkova et al., *J Biol Chem* 284:26557-68 (2009)) and Cys244 in gingipain R (Eichinger, et al., *EMBO J.* 18:5453-62 (1999)) (FIGS. 5A-5B). Genetic disruption of this S-nitrosylation motif in TcdB by site-directed mutagenesis of Glu743 to alanine diminished the ability of GSNO to transnitrosylate the toxin (FIG. 5Q). However, site-directed mutagenesis of the catalytic His653 to alanine in TcdB played a relatively minor role in this transnitrosylation reaction (FIG. 5C). This observation is consistent with the unusually large distances (>6 Å) between the catalytic cysteine and histidine in all of the toxin cysteine protease crystal structures (Pruitt et al., *J Biol Chem* 284: 21934-40 (2009)). It is more likely that this histidine residue plays a role in substrate orientation within the active site rather than conferring nucleophilicity to the cysteine thiolate, with the catalytic aspartic acid stabilizing the histidine imidazolium ring (FIG. 5D). Site-directed mutagenesis of His to alanine in TcdB confirmed its role in this catalytic activity (FIG. 5E). Moreover, a potential regulatory role for Glu743 in the cysteine protease active site is predicted via hydrogen bonding and modulation of catalytic cysteine thiolate reactivity (FIG. 5D). Mutagenesis of Glu743 to alanine in TcdB confirmed its role in actively regulating toxin self-cleavage in the presence of inositol phosphate cofactor (FIGS. 5E-5G). Thus, this highly conserved regulatory residue appears to facilitate an allosteric-switch mechanism (Cui et al., *Protein Science* 17:1295-1307 (2008)), possibly to restrict toxin self-cleavage in response to situational exposure to $InsP_6$ cofactor which can reach micromolar concentrations in the extracellular gut environment from dietary sources (Bohn et al., *J Zhejiang Univ Sci B* 9:165-191 (2008); Letcher et al., *Biochem J*416:261-270 (2008)).

Therapeutic Allostery of the *C. difficile* Toxins. Metronidazole and vancomycin can effectively treat *C. difficile* infection, but the association of these drugs with high relapse rates represents a major health problem. These considerations necessitate the development of alternative non-antibiotic therapeutic strategies that can inactivate the exotoxin activity. The observation that S-nitrosylation inhibits toxin self-cleavage and that GSNO likely serves as the endogenous S-nitrosylating agent prompted the testing of whether GSNO can be exploited therapeutically to confer protection against *C. difficile* infection.

Figure 6A:
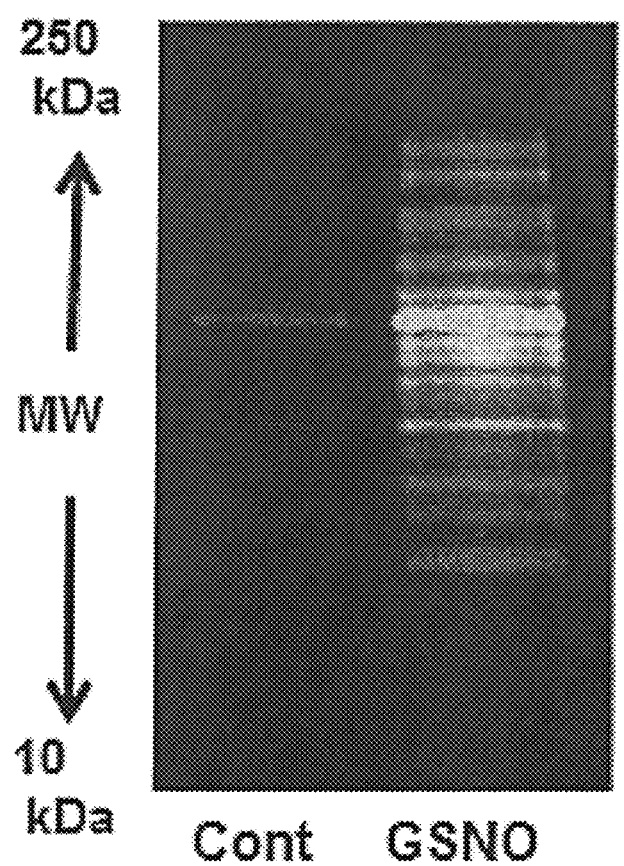
FIGS. 6A-6F. GSNO based therapy for *Clostridium difficile* infection.
Figure 6B:
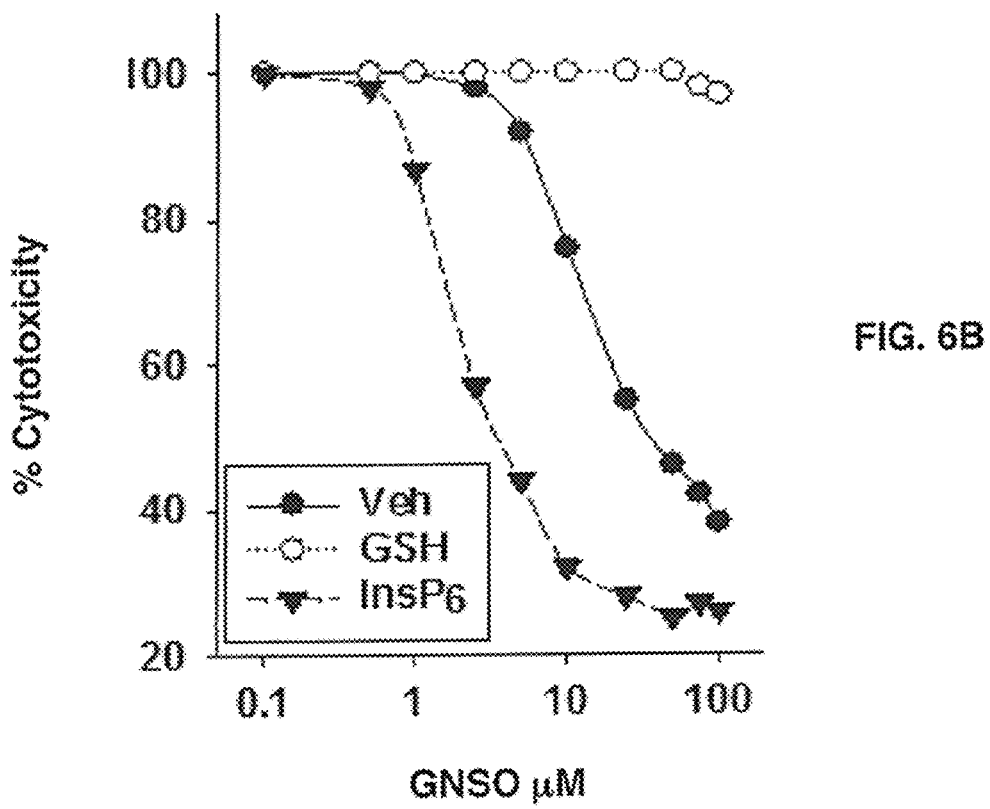
Figure 6C:
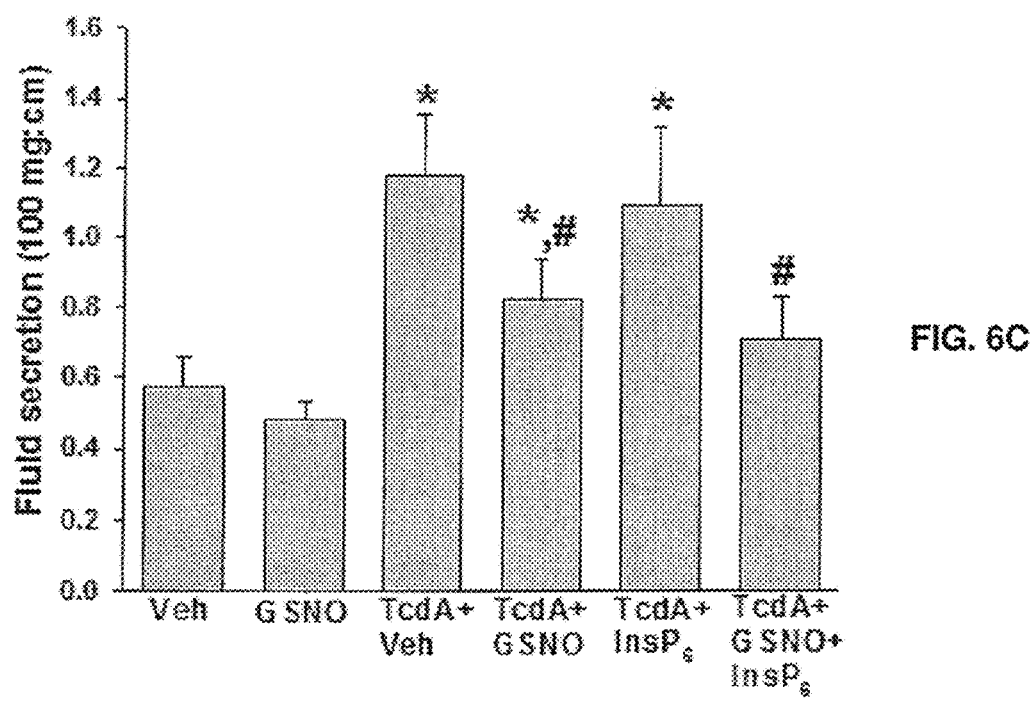
Figure 6D:
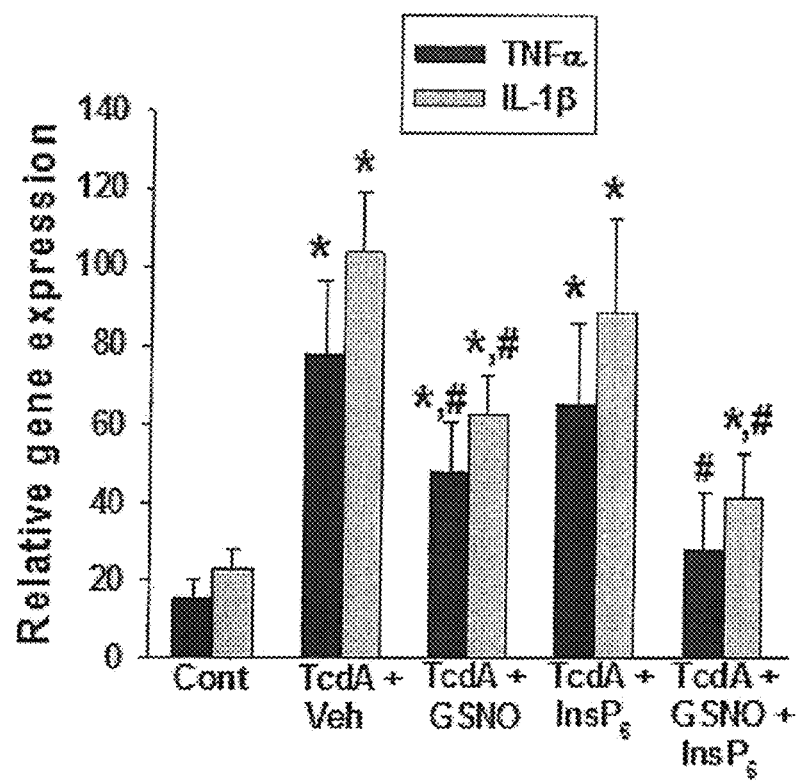

In vitro studies demonstrated that exogenous GSNO dose-dependently S-nitrosylated epithelial cell proteins (FIG. 6A), and prevented cytotoxicity in Caco-2 cells with a half-maximum inhibition concentration ($IC_{50}$) of 57.9+13.7 and 46.3+7.1 µM for TcdA and TcdB, respectively (FIG. 6B). Inhibition of toxin activity was reversed by GSH- or dithiothreitol-mediated protein denitrosylation, and cytoprotection was greatly enhanced by the addition of inositolphosphate cofactor, which reduced the IC$_{50}$ of GSNO into the low micromolar range (FIG. 6B). Using the Cd-1 murine loop model, exogenous GSNO markedly reduced toxin-induced disease activity, including a significant inhibition of histological damage, inflammation and intestinal secretion when co-injected with TcdA into ileal loops for 4 hrs (FIGS. 6C-6D). In addition, as was evident in the in vitro studies, InsP$_6$ enhanced the therapeutic actions of exogenous S-nitrosothiol in vivo (FIGS. 6C-6D).

Figure 6E:
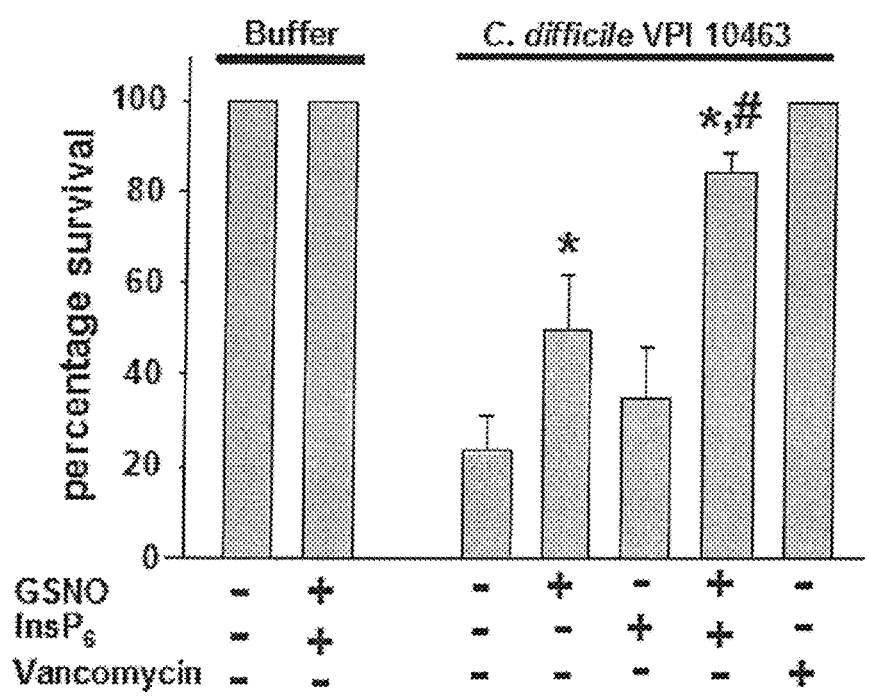
Figure 6F:
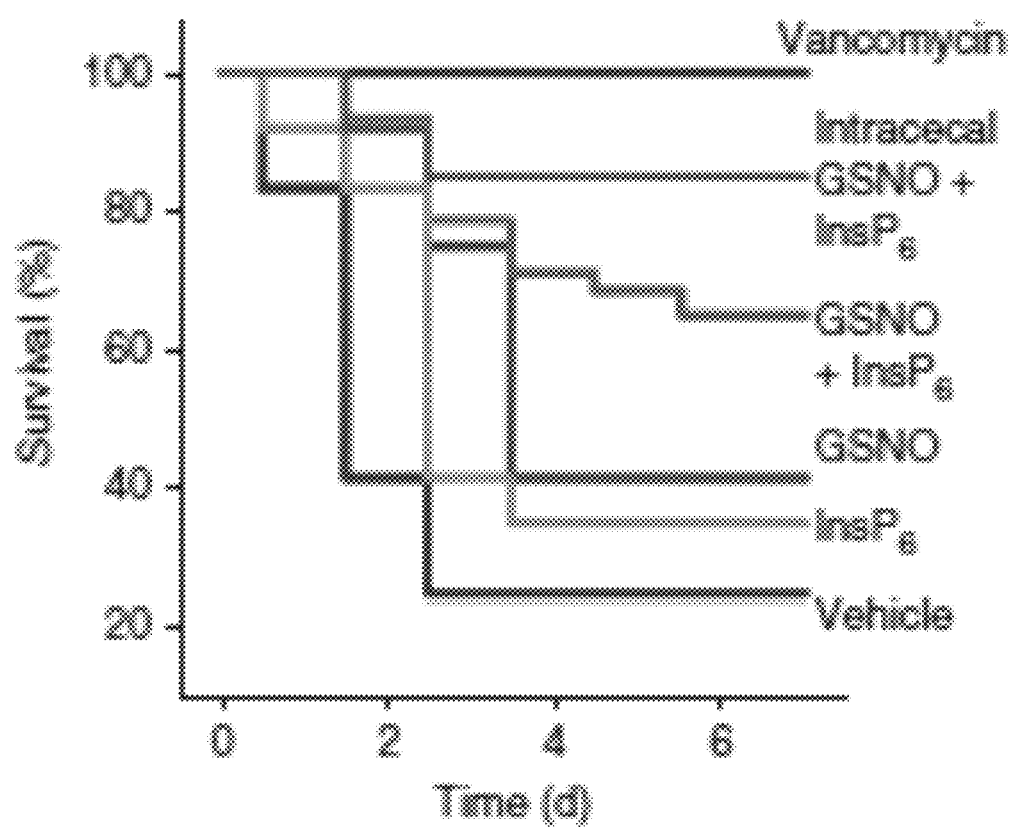

The therapeutic efficacy of GSNO was also tested in a murine infectious disease model that closely mimics the human disease (Chen et al., *Gastroenterology* 135:1984-92 (2008)). Kaplan-Merier survival plots of infected mice demonstrated a survival benefit of GSNO that was potentiated by InsP$_6$ (FIG. 6E). Thus, the most significant protection was evident in animals that received both oral GSNO and InsP$_6$, and this was potentiated further by direct therapeutic delivery into the cecum (FIGS. 6E-6F). Synergistic benefits of GSNO and InsP$_6$ identify the toxin as a primary locus of GSNO action.

---

The invention claimed is:

1. A method for ameliorating the pathophysiology of an infection with a bacterium producing a microbial cysteine protease exotoxin in a subject comprising, administering to gastrointestinal tract of the subject an effective dose of a nitrosylated inositol phosphate having a chemical structure of Formula I:

Formula I where at $R_1$-$R_6$ independently are hydrogen or —PO(OH)$_2$ NO, wherein at least one of $R_1$-$R_6$ is —PO(OH)$_2$ NO.

2. The method of claim 1, wherein the exotoxin is a *Clostridium* exotoxin.

3. The method of claim 2, wherein the exotoxin is a *Clostridium difficile*, *Clostridium sordellii*, *Clostridium novyi*, *Clostridium botulinum*, *Clostridium perfringens*, or *Clostridium tetani* exotoxin.

4. The method of claim 1, wherein the exotoxin is *Vibrio cholera* RTX, gingipains, CPD$_{MARTX}$, or CDP$_{adh}$ exotoxin.

5. The method of claim 1, wherein the nitrosylated inositol phosphate is administered in an amount of about 1 µM to about 10 mM.

* * * * *

SEQUENCE LISTING

```
<160> NUMBER OF SEQ ID NOS: 7

<210> SEQ ID NO 1
<211> LENGTH: 2084
<212> TYPE: PRT
<213> ORGANISM: Clostridium difficile

<400> SEQUENCE: 1

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Asn Glu Asn Lys Tyr Leu Gln Leu
            35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285
```

```
Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Glu Ala Gly Ser
                565                 570                 575

Lys Asn Tyr Val His Tyr Ile Ile Gln Leu Gln Gly Asp Asp Ile Ser
                580                 585                 590

Tyr Glu Ala Thr Cys Asn Leu Phe Ser Lys Asn Pro Lys Asn Ser Ile
    595                 600                 605

Ile Ile Gln Arg Asn Met Asn Glu Ser Ala Lys Ser Tyr Phe Leu Ser
610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
```

-continued

```
                705                 710                 715                 720
Ile Met Asp Lys Ile Thr Ser Thr Leu Pro Asp Val Asn Lys Asn Ser
                    725                 730                 735
Ile Thr Ile Gly Ala Asn Gln Tyr Glu Val Arg Ile Asn Ser Glu Gly
                    740                 745                 750
Arg Lys Glu Leu Leu Ala His Ser Gly Lys Trp Ile Asn Lys Glu Glu
                    755                 760                 765
Ala Ile Met Ser Asp Leu Ser Ser Lys Glu Tyr Ile Phe Phe Asp Ser
                    770                 775                 780
Ile Asp Asn Lys Leu Lys Ala Lys Ser Lys Asn Ile Pro Gly Leu Ala
785                 790                 795                 800
Ser Ile Ser Glu Asp Ile Lys Thr Leu Leu Leu Asp Ala Ser Val Ser
                    805                 810                 815
Pro Asp Thr Lys Phe Ile Leu Asn Asn Leu Lys Leu Asn Ile Glu Ser
                    820                 825                 830
Ser Ile Gly Asp Tyr Ile Tyr Tyr Glu Lys Leu Glu Pro Val Lys Asn
                    835                 840                 845
Ile Ile His Asn Ser Ile Asp Asp Leu Ile Asp Glu Phe Asn Leu Leu
                    850                 855                 860
Glu Asn Val Ser Asp Glu Leu Tyr Glu Leu Lys Lys Leu Asn Asn Leu
865                 870                 875                 880
Asp Glu Lys Tyr Leu Ile Ser Phe Glu Asp Ile Ser Lys Asn Asn Ser
                    885                 890                 895
Thr Tyr Ser Val Arg Phe Ile Asn Lys Ser Asn Gly Glu Ser Val Tyr
                    900                 905                 910
Val Glu Thr Glu Lys Glu Ile Phe Ser Lys Tyr Ser Glu His Ile Thr
                    915                 920                 925
Lys Glu Ile Ser Thr Ile Lys Asn Ser Ile Ile Thr Asp Val Asn Gly
                    930                 935                 940
Asn Leu Leu Asp Asn Ile Gln Leu Asp His Thr Ser Gln Val Asn Thr
945                 950                 955                 960
Leu Asn Ala Ala Phe Phe Ile Gln Ser Leu Ile Asp Tyr Ser Ser Asn
                    965                 970                 975
Lys Asp Val Leu Asn Asp Leu Ser Thr Ser Val Lys Val Gln Leu Tyr
                    980                 985                 990
Ala Gln Leu Phe Ser Thr Gly Leu Asn Thr Ile Tyr Asp Ser Ile Gln
                    995                 1000                1005
Leu Val Asn Leu Ile Ser Asn Ala Val Asn Asp Thr Ile Asn Val
            1010                1015                1020
Leu Pro Thr Ile Thr Glu Gly Ile Pro Ile Val Ser Thr Ile Leu
            1025                1030                1035
Asp Gly Ile Asn Leu Gly Ala Ala Ile Lys Glu Leu Leu Asp Glu
            1040                1045                1050
His Asp Pro Leu Leu Lys Lys Glu Leu Glu Ala Lys Val Gly Val
            1055                1060                1065
Leu Ala Ile Asn Met Ser Leu Ser Ile Ala Ala Thr Val Ala Ser
            1070                1075                1080
Ile Val Gly Ile Gly Ala Glu Val Thr Ile Phe Leu Leu Pro Ile
            1085                1090                1095
Ala Gly Ile Ser Ala Gly Ile Pro Ser Leu Val Asn Asn Glu Leu
            1100                1105                1110
Ile Leu His Asp Lys Ala Thr Ser Val Val Asn Tyr Phe Asn His
            1115                1120                1125
```

-continued

Leu Ser Glu Ser Lys Lys Tyr Gly Pro Leu Lys Thr Glu Asp Asp
    1130                1135                1140

Lys Ile Leu Val Pro Ile Asp Asp Leu Val Ile Ser Glu Ile Asp
    1145                1150                1155

Phe Asn Asn Asn Ser Ile Lys Leu Gly Thr Cys Asn Ile Leu Ala
    1160                1165                1170

Met Glu Gly Gly Ser Gly His Thr Val Thr Gly Asn Ile Asp His
    1175                1180                1185

Phe Phe Ser Ser Pro Ser Ile Ser Ser His Ile Pro Ser Leu Ser
    1190                1195                1200

Ile Tyr Ser Ala Ile Gly Ile Glu Thr Glu Asn Leu Asp Phe Ser
    1205                1210                1215

Lys Lys Ile Met Met Leu Pro Asn Ala Pro Ser Arg Val Phe Trp
    1220                1225                1230

Trp Glu Thr Gly Ala Val Pro Gly Leu Arg Ser Leu Glu Asn Asp
    1235                1240                1245

Gly Thr Arg Leu Leu Asp Ser Ile Arg Asp Leu Tyr Pro Gly Lys
    1250                1255                1260

Phe Tyr Trp Arg Phe Tyr Ala Phe Phe Asp Tyr Ala Ile Thr Thr
    1265                1270                1275

Leu Lys Pro Val Tyr Glu Asp Thr Asn Ile Lys Ile Lys Leu Asp
    1280                1285                1290

Lys Asp Thr Arg Asn Phe Ile Met Pro Thr Ile Thr Thr Asn Glu
    1295                1300                1305

Ile Arg Asn Lys Leu Ser Tyr Ser Phe Asp Gly Ala Gly Gly Thr
    1310                1315                1320

Tyr Ser Leu Leu Leu Ser Ser Tyr Pro Ile Ser Thr Asn Ile Asn
    1325                1330                1335

Leu Ser Lys Asp Asp Leu Trp Ile Phe Asn Ile Asp Asn Glu Val
    1340                1345                1350

Arg Glu Ile Ser Ile Glu Asn Gly Thr Ile Lys Lys Gly Lys Leu
    1355                1360                1365

Ile Lys Asp Val Leu Ser Lys Ile Asp Ile Asn Lys Asn Lys Leu
    1370                1375                1380

Ile Ile Gly Asn Gln Thr Ile Asp Phe Ser Gly Asp Ile Asp Asn
    1385                1390                1395

Lys Asp Arg Tyr Ile Phe Leu Thr Cys Glu Leu Asp Asp Lys Ile
    1400                1405                1410

Ser Leu Ile Ile Glu Ile Asn Leu Val Ala Lys Ser Tyr Ser Leu
    1415                1420                1425

Leu Leu Ser Gly Asp Lys Asn Tyr Leu Ile Ser Asn Leu Ser Asn
    1430                1435                1440

Thr Ile Glu Lys Ile Asn Thr Leu Gly Leu Asp Ser Lys Asn Ile
    1445                1450                1455

Ala Tyr Asn Tyr Thr Asp Glu Ser Asn Asn Lys Tyr Phe Gly Ala
    1460                1465                1470

Ile Ser Lys Thr Ser Gln Lys Ser Ile Ile His Tyr Lys Lys Asp
    1475                1480                1485

Ser Lys Asn Ile Leu Glu Phe Tyr Asn Asp Ser Thr Leu Glu Phe
    1490                1495                1500

Asn Ser Lys Asp Phe Ile Ala Glu Asp Ile Asn Val Phe Met Lys
    1505                1510                1515

-continued

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
1550                1555                1560

Ser Tyr Leu Asp Phe Val Lys Asn Ser Asp Gly His His Asn Thr
1565                1570                1575

Ser Asn Phe Met Asn Leu Phe Leu Asp Asn Ile Ser Phe Trp Lys
1580                1585                1590

Leu Phe Gly Phe Glu Asn Ile Asn Phe Val Ile Asp Lys Tyr Phe
1595                1600                1605

Thr Leu Val Gly Lys Thr Asn Leu Gly Tyr Val Glu Phe Ile Cys
1610                1615                1620

Asp Asn Asn Lys Asn Ile Asp Ile Tyr Phe Gly Glu Trp Lys Thr
1625                1630                1635

Ser Ser Ser Lys Ser Thr Ile Phe Ser Gly Asn Gly Arg Asn Val
1640                1645                1650

Val Val Glu Pro Ile Tyr Asn Pro Asp Thr Gly Glu Asp Ile Ser
1655                1660                1665

Thr Ser Leu Asp Phe Ser Tyr Glu Pro Leu Tyr Gly Ile Asp Arg
1670                1675                1680

Tyr Ile Asn Lys Val Leu Ile Ala Pro Asp Leu Tyr Thr Ser Leu
1685                1690                1695

Ile Asn Ile Asn Thr Asn Tyr Tyr Ser Asn Glu Tyr Tyr Pro Glu
1700                1705                1710

Ile Ile Val Leu Asn Pro Asn Thr Phe His Lys Lys Val Asn Ile
1715                1720                1725

Asn Leu Asp Ser Ser Ser Phe Glu Tyr Lys Trp Ser Thr Glu Gly
1730                1735                1740

Ser Asp Phe Ile Leu Val Arg Tyr Leu Glu Glu Ser Asn Lys Lys
1745                1750                1755

Ile Leu Gln Lys Ile Arg Ile Lys Gly Ile Leu Ser Asn Thr Gln
1760                1765                1770

Ser Phe Asn Lys Met Ser Ile Asp Phe Lys Asp Ile Lys Lys Leu
1775                1780                1785

Ser Leu Gly Tyr Ile Met Ser Asn Phe Lys Ser Phe Asn Ser Glu
1790                1795                1800

Asn Glu Leu Asp Arg Asp His Leu Gly Phe Lys Ile Ile Asp Asn
1805                1810                1815

Lys Thr Tyr Tyr Tyr Asp Glu Asp Ser Lys Leu Val Lys Gly Leu
1820                1825                1830

Ile Asn Ile Asn Asn Ser Leu Phe Tyr Phe Asp Pro Ile Glu Phe
1835                1840                1845

Asn Leu Val Thr Gly Trp Gln Thr Ile Asn Gly Lys Lys Tyr Tyr
1850                1855                1860

Phe Asp Ile Asn Thr Gly Ala Ala Leu Thr Ser Tyr Lys Ile Ile
1865                1870                1875

Asn Gly Lys His Phe Tyr Phe Asn Asn Asp Gly Val Met Gln Leu
1880                1885                1890

Gly Val Phe Lys Gly Pro Asp Gly Phe Glu Tyr Phe Ala Pro Ala
1895                1900                1905

Asn Thr Gln Asn Asn Asn Ile Glu Gly Gln Ala Ile Val Tyr Gln

Ser Lys Phe Leu Thr Leu Asn Gly Lys Lys Tyr Tyr Phe Asp Asn
1925                1930                1935

Asp Ser Lys Ala Val Thr Gly Trp Arg Ile Ile Asn Asn Glu Lys
1940                1945                1950

Tyr Tyr Phe Asn Pro Asn Asn Ala Ile Ala Ala Val Gly Leu Gln
1955                1960                1965

Val Ile Asp Asn Asn Lys Tyr Tyr Phe Asn Pro Asp Thr Ala Ile
1970                1975                1980

Ile Ser Lys Gly Trp Gln Thr Val Asn Gly Ser Arg Tyr Tyr Phe
1985                1990                1995

Asp Thr Asp Thr Ala Ile Ala Phe Asn Gly Tyr Lys Thr Ile Asp
2000                2005                2010

Gly Lys His Phe Tyr Phe Asp Ser Asp Cys Val Val Lys Ile Gly
2015                2020                2025

Val Phe Ser Thr Ser Asn Gly Phe Glu Tyr Phe Ala Pro Ala Asn
2030                2035                2040

Thr Tyr Asn Asn Asn Ile Glu Gly Gln Ala Ile Val Tyr Gln Ser
2045                2050                2055

Lys Phe Leu Thr Leu Asn Gly Lys Lys Tyr Tyr Phe Asp Asn Asn
2060                2065                2070

Ser Lys Ala Val Thr Gly Trp Gln Thr Ile Asp
2075                2080

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
gccgtggctc tcttggc                                                  17

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gcactccttg gcaaaactgc                                               20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
atgagcacag aaagcatgat c                                             21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

```
<400> SEQUENCE: 5
tacaggcttg tcactcgaat t                                              21

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
ttgacggacc ccaaaagatg                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
agaaggtgct catgtcctca                                                20
```